(12) United States Patent
Schaeffer et al.

(10) Patent No.: US 10,398,844 B2
(45) Date of Patent: Sep. 3, 2019

(54) CONTROLLED INJECTION DEVICES, SYSTEMS, AND METHODS

(71) Applicant: Cook Medical Technologies LLC, Bloomington, IN (US)

(72) Inventors: Darin Schaeffer, Bloomington, IN (US); Daniel Dalenberg, Portage, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 1139 days.

(21) Appl. No.: 14/068,080

(22) Filed: Oct. 31, 2013

(65) Prior Publication Data

US 2014/0128841 A1 May 8, 2014

Related U.S. Application Data

(60) Provisional application No. 61/721,557, filed on Nov. 2, 2012.

(51) Int. Cl.
*A61M 5/31* (2006.01)
*A61M 5/315* (2006.01)
*A61B 17/88* (2006.01)
*A61B 90/00* (2016.01)

(52) U.S. Cl.
CPC ..... *A61M 5/31511* (2013.01); *A61B 17/8808* (2013.01); *A61B 17/8822* (2013.01); *A61B 2090/036* (2016.02)

(58) Field of Classification Search
CPC .......... A61M 5/31511; A61M 5/31515; A61M 5/28; A61M 5/31505; A61M 5/3158; A61B 17/8822; A61B 17/3472; A61B 17/8833; B01F 13/002
See application file for complete search history.

(56) References Cited

U.S. PATENT DOCUMENTS

| 2,233,554 | A | | 3/1941 | Pletcher | |
|---|---|---|---|---|---|
| 3,122,280 | A | * | 2/1964 | Goda | A61M 1/00 222/309 |
| 3,598,120 | A | | 8/1971 | Mass | |
| 3,732,872 | A | * | 5/1973 | Lakritz | A24C 5/608 131/300 |
| 3,811,441 | A | * | 5/1974 | Sarnoff | A61M 5/24 604/201 |
| 3,819,091 | A | | 6/1974 | Hollender | |
| 4,073,321 | A | | 2/1978 | Moskowitz | |

(Continued)

OTHER PUBLICATIONS

The International Searching Authority, International Search Report and the Written Opinion, dated Feb. 26, 2014, for International Application No. PCT/US2013/067652.

(Continued)

*Primary Examiner* — Scott J Medway
(74) *Attorney, Agent, or Firm* — Buchanan Van Tuinen LLC

(57) ABSTRACT

Medical devices are described herein. More particularly, the disclosure relates to controlled injection devices, systems, and methods used for the introduction of treatment material into a cavity. An exemplary controlled injection system comprises an injection device and a jig. The jig is adapted to receive the injection device and has a jig head, jig shaft, and a jig housing.

15 Claims, 13 Drawing Sheets

(56) References Cited

U.S. PATENT DOCUMENTS

| | | | |
|---|---|---|---|
| 4,091,812 A * | 5/1978 | Helixon | A61M 5/3156 604/208 |
| 4,231,368 A * | 11/1980 | Becker | A61M 5/20 604/117 |
| 4,429,724 A | 2/1984 | Dorros et al. | |
| 4,546,767 A | 10/1985 | Smith | |
| 4,563,178 A | 1/1986 | Santeramo | |
| 4,594,073 A * | 6/1986 | Stine | A61B 10/0283 600/578 |
| 4,766,907 A * | 8/1988 | de Groot | A61B 10/02 600/567 |
| 4,883,101 A * | 11/1989 | Strong | A61M 5/1782 141/27 |
| 5,115,816 A * | 5/1992 | Lee | A61M 5/1782 600/562 |
| 5,241,969 A * | 9/1993 | Carson | A61B 10/0283 600/566 |
| 5,417,660 A * | 5/1995 | Martin | A61M 5/3271 604/110 |
| 5,469,860 A * | 11/1995 | De Santis | A61B 10/0283 600/562 |
| 5,509,904 A * | 4/1996 | Kilham | A61M 5/20 604/192 |
| 5,591,188 A * | 1/1997 | Waisman | A61B 17/3472 604/157 |
| 6,416,323 B1 * | 7/2002 | Grenfell | A61M 5/3271 433/90 |
| 6,425,897 B2 | 7/2002 | Overes et al. | |
| 6,595,388 B2 | 7/2003 | Mizutani et al. | |
| 7,118,556 B2 * | 10/2006 | Nerney | A61M 5/3148 604/181 |
| 7,329,241 B2 | 2/2008 | Horvath et al. | |
| 7,338,471 B2 | 3/2008 | Bates | |
| 7,632,262 B2 | 12/2009 | Bates | |
| 7,862,551 B2 | 1/2011 | Bates | |
| 8,282,648 B2 | 10/2012 | Tekulve | |
| 8,540,123 B2 | 9/2013 | Melsheimer et al. | |
| 9,795,734 B2 * | 10/2017 | McLoughlin | A61M 5/14546 |
| 2003/0018339 A1 * | 1/2003 | Higueras et al. | 606/93 |
| 2004/0167476 A1 * | 8/2004 | Westbye | A61M 5/5013 604/192 |
| 2004/0254538 A1 | 12/2004 | Murphy et al. | |
| 2009/0043263 A1 | 2/2009 | Woodard, Jr. et al. | |
| 2010/0282774 A1 | 11/2010 | Greter et al. | |
| 2011/0178500 A1 * | 7/2011 | Shang | A61M 5/2033 604/506 |
| 2012/0195157 A1 | 8/2012 | McKay | |
| 2012/0245590 A1 | 9/2012 | Melsheimer et al. | |
| 2013/0158559 A1 | 6/2013 | Schaeffer | |
| 2015/0165135 A1 * | 6/2015 | McLoughlin | A61M 5/3134 604/111 |
| 2017/0296753 A1 * | 10/2017 | Rowe | A61M 5/31515 |

OTHER PUBLICATIONS

International Searching Authority, "International Preliminary Report on Patentability," for International application No. PCT/US2013/067652, dated May 14, 2015, pp. 1-11.

* cited by examiner

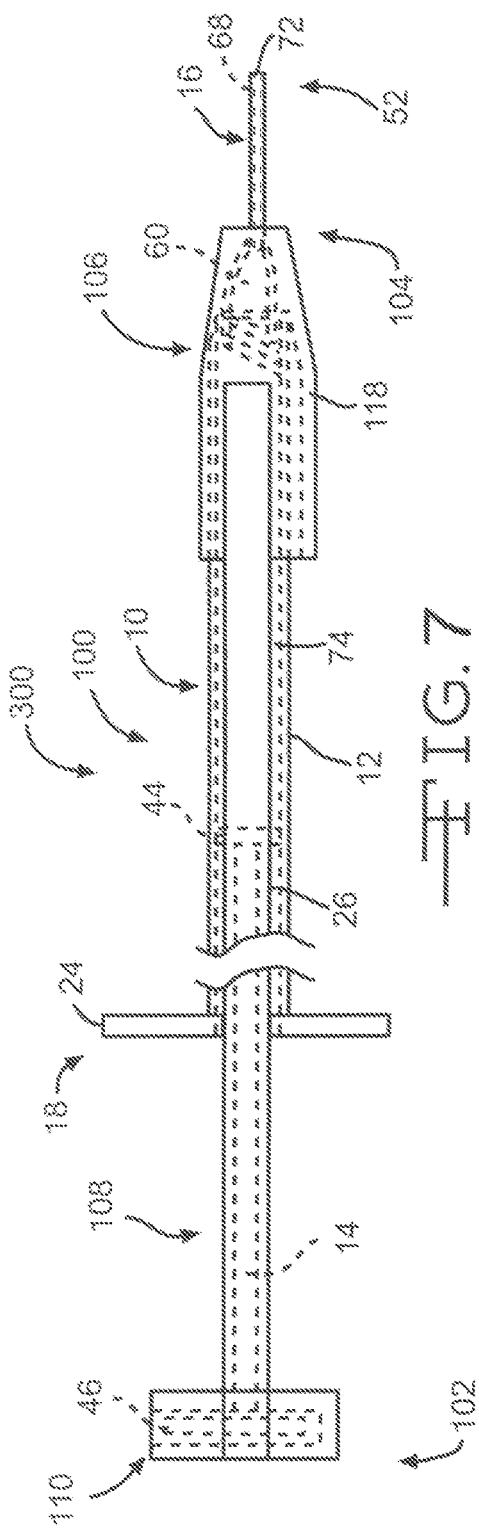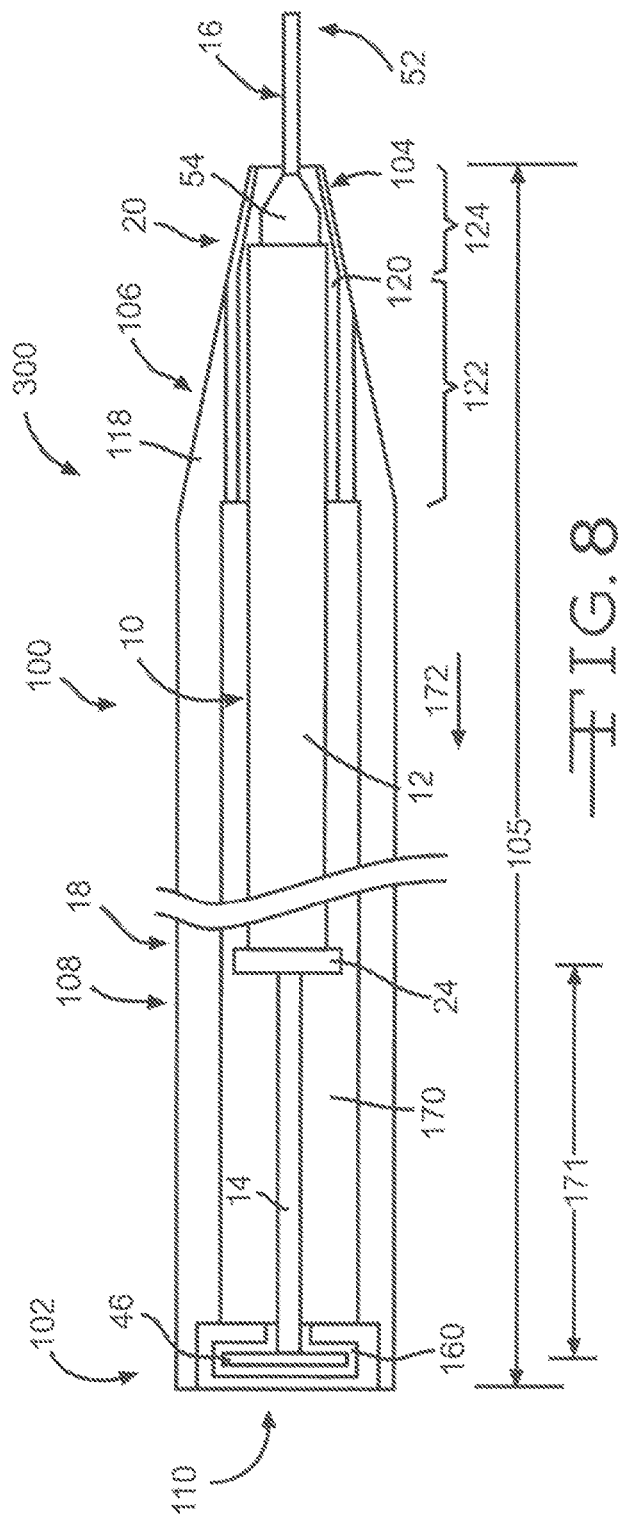

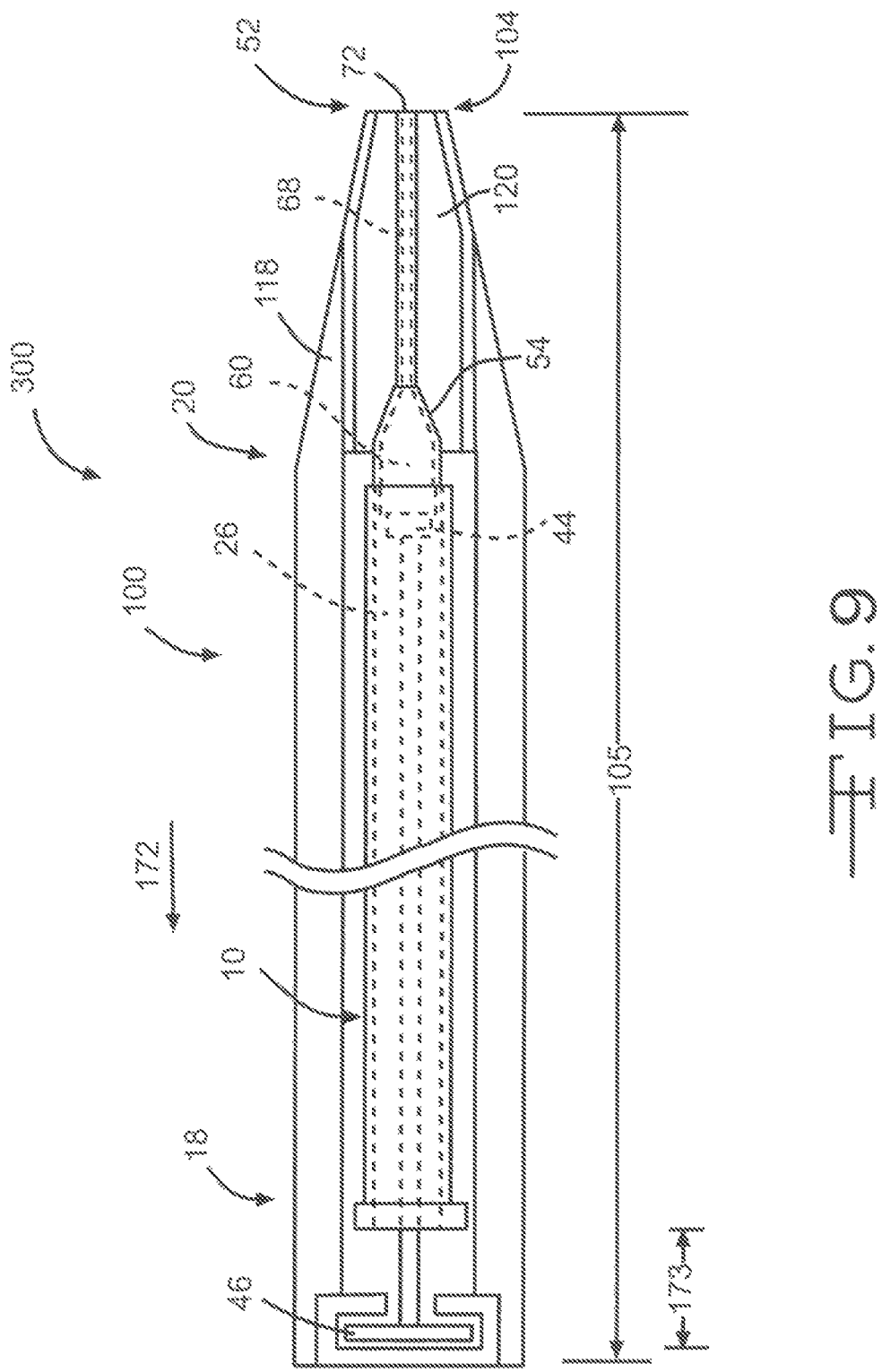

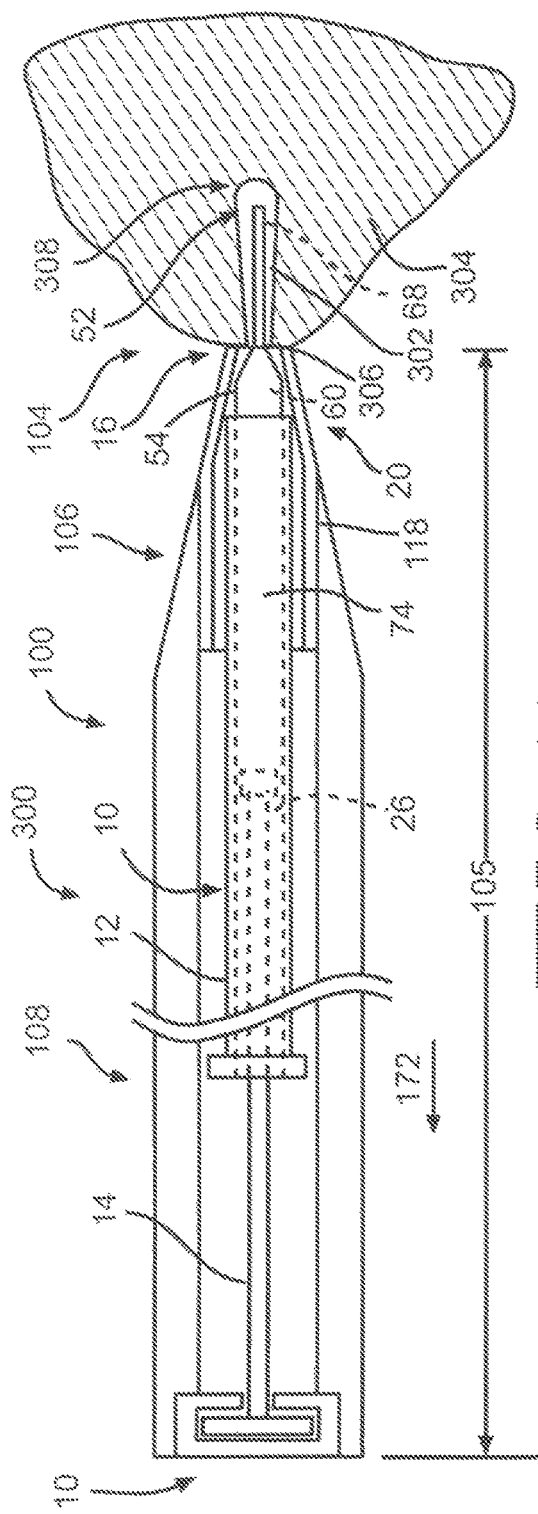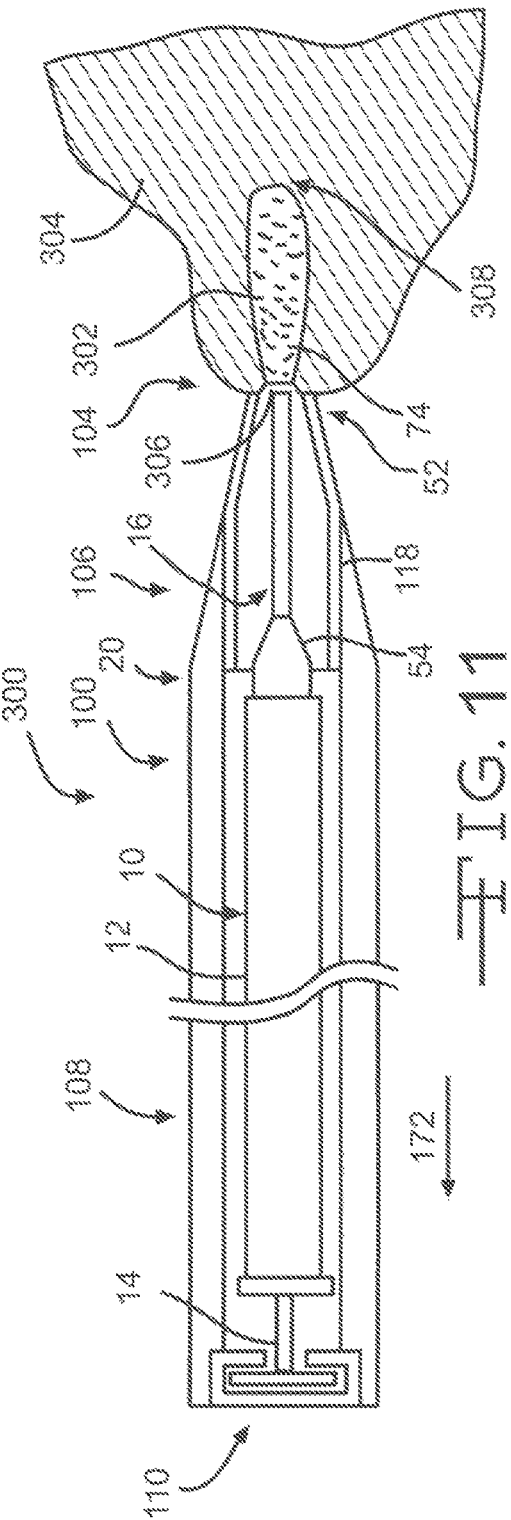

CONTROLLED INJECTION DEVICES, SYSTEMS, AND METHODS

RELATED APPLICATIONS

This application claims the benefit of U.S. Provisional Application No. 61/721,557, filed on Nov. 2, 2012. The entire contents of this related application are hereby incorporated into this disclosure by reference.

FIELD

The disclosure relates generally to medical devices. More particularly, the disclosure relates to controlled injection devices and systems used for the introduction of a treatment material into a cavity. The disclosure also relates to methods of introducing a treatment material into a cavity.

BACKGROUND

During the performance of a medical procedure, it is sometimes necessary, or otherwise desirable, to create a cavity within a bone to receive a medical device or create a passageway that can be used to navigate a medical device towards a point of treatment. For example, in orthopedic procedures, a cavity is sometimes created in a bone to receive a prosthetic component that is attached to the bone within the cavity using bone cement. Alternatively, if a passageway has been created to navigate a medical device towards a point of treatment, bone cement is sometimes used to close the cavity subsequent to completing the procedure.

Bone cement is generally introduced into a cavity using a conventional syringe such that it flows from the center of the cavity and radially outward to the cavity wall. While introducing the bone cement, the needle of the syringe is withdrawn at a continuous rate from the cavity such that the tip of the needle is at or near the meniscus of the cement that has already been introduced into the cavity. This provides a continuous and substantially uninterrupted flow of cement and is generally accomplished by manually withdrawing the needle from the cavity while simultaneously injecting the cement by depressing the plunger of the syringe. Manually withdrawing the needle from the cavity, however, has significant drawbacks. For example, it is sometimes difficult to visualize the bottom of the cavity and/or the meniscus of the bone cement as it is being introduced into the cavity due to the needle obstructing the view of the cavity and/or cement. Therefore, manual withdrawal of the needle requires an individual using the syringe to approximate the rate at which the syringe should be withdrawn from the cavity and the rate at which the plunger of the syringe should be depressed to introduce an appropriate amount of bone cement into the cavity.

Therefore, a need exists for improved controlled injection devices, systems, and methods for introducing a treatment material into a cavity.

SUMMARY

Various exemplary controlled injection systems are described.

A first exemplary controlled injection system comprises an injection device and a jig. The injection device has a barrel, a plunger partially disposed within the barrel, and a needle attached to the barrel. The jig has a jig proximal end and a jig distal end and comprises a jig head, a jig shaft, and a jig plunger housing. The jig head has a head proximal end, head distal end, and a head body that defines a head opening adapted to receive a portion of the injection device. The head opening extends from the head proximal end to the head distal end. The jig shaft extends from the jig head and towards the jig proximal end. The jig shaft has a shaft proximal end and a shaft distal end. The jig plunger housing is disposed on the jig shaft and has a plunger housing proximal end, plunger housing distal end, and a plunger housing body that defines a plunger housing recess that extends into the plunger housing body. The plunger housing recess is adapted to receive a portion of the plunger.

A second exemplary controlled injection system comprises an injection device and a jig. The injection device has a barrel, a plunger partially disposed within the barrel, and a needle attached to the barrel. The jig has a jig proximal end and a jig distal end and comprises a jig head, a jig shaft, and a jig plunger housing. The jig head has a head proximal end, head distal end, and a head body that defines a head opening adapted to receive a portion of the injection device. The head opening extends from the head proximal end to the head distal end. The jig shaft extends from the jig head and towards the jig proximal end. The jig shaft has a shaft proximal end and a shaft distal end. The jig plunger housing is disposed on the jig shaft and has a plunger housing proximal end, plunger housing distal end, and a plunger housing body that defines a plunger housing recess that extends into the plunger housing body. The plunger housing recess is adapted to receive a portion of the plunger and has a plunger housing recess first portion and a plunger housing recess second portion. The plunger housing recess first portion extends from the plunger housing distal end towards the plunger housing proximal end. The plunger housing recess second portion extends from the plunger housing first portion towards the plunger housing proximal end. The plunger housing recess first portion comprises a plunger housing first width measured along the plunger housing distal end. The plunger housing recess second portion comprises a plunger housing second width measured along the plunger housing distal end. The plunger housing first width is different from the plunger housing second width.

A third exemplary controlled injection system comprises an injection device and a jig. The injection device has a barrel, a plunger partially disposed within the barrel, and a needle attached to the barrel. The jig has a jig proximal end and a jig distal end and comprises a jig head, a jig shaft, and a jig plunger housing. The jig head has a head proximal end, head distal end, and a head body that defines a head opening adapted to receive a portion of the injection device. The head opening extends from the head proximal end to the head distal end. The jig shaft extends from the jig head and towards the jig proximal end. The jig shaft has a shaft proximal end and a shaft distal end. The jig plunger housing is disposed on the jig shaft and has a plunger housing proximal end, plunger housing distal end, and a plunger housing body that defines a plunger housing recess that extends into the plunger housing body. The plunger housing recess is adapted to receive a portion of the plunger and has a plunger housing recess first portion and a plunger housing recess second portion. The plunger housing recess first portion extends from the plunger housing distal end towards the plunger housing proximal end. The plunger housing recess second portion extends from the plunger housing first portion towards the plunger housing proximal end. The plunger housing recess first portion comprises a plunger housing first width measured along the plunger housing distal end. The plunger housing recess second portion comprises a plunger housing second width measured along the plunger housing distal end. The plunger housing second width is greater than the plunger housing first width.

In addition, various methods of introducing a treatment material into a cavity are described.

A first exemplary method of introducing a treatment material into a cavity having a cavity wall comprises the steps of: inserting an injection device that has an injection device proximal end, an injection device distal end, a barrel containing the treatment material, a needle, and a plunger, into a jig having a jig proximal end and a jig distal end such that the injection device distal end is disposed distal to the jig distal end and the plunger is fixed relative to the jig; advancing the injection device distal end into the cavity; advancing the jig towards the cavity wall such that it contacts the cavity wall; applying a proximal force on the barrel such that the barrel moves proximally with respect to the jig; and stopping the application of a proximal force on the barrel.

A second exemplary method of introducing a treatment material into a cavity formed in a bone comprises the steps of: inserting an injection device that has an injection device proximal end, an injection device distal end, a barrel containing the treatment material, a needle, and a plunger, into a jig having a jig proximal end and a jig distal end such that the injection device distal end is disposed distal to the jig distal end and the plunger is fixed relative to the jig; advancing the injection device distal end into the cavity; advancing the jig towards the cavity wall such that it contacts the bone; applying a proximal force on the barrel such that the barrel moves proximally with respect to the jig; and stopping the application of a proximal force on the barrel.

A third exemplary method of introducing a treatment material into a bodily passage having a passage wall comprises the steps of: inserting an injection device that has an injection device proximal end, an injection device distal end, a barrel containing the treatment material, a needle, and a plunger, into a jig having a jig proximal end and a jig distal end such that the injection device distal end is disposed distal to the jig distal end and the plunger is fixed relative to the jig; advancing the injection device distal end into the bodily passage; advancing the jig towards the passage wall such that it contacts the passage wall; applying a proximal force on the barrel such that the barrel moves proximally with respect to the jig; and stopping the application of a proximal force on the barrel.

Additional understanding of the exemplary controlled injection devices, systems and methods can be obtained by review of the detailed description, below, and the appended drawings.

BRIEF DESCRIPTION OF THE FIGURES

FIG. 7 is a side view of the controlled injection system illustrated in FIG. 6 in the first configuration.

FIG. 8 is a top view of the controlled injection system illustrated in FIG. 6 in the first configuration.

FIG. 9 is a top view of the controlled injection system illustrated in FIG. 6 in the second configuration.

FIG. 10 is a top view of the controlled injection system illustrated in FIG. 6 in the first configuration and partially disposed in a cavity.

FIG. 11 is a top view of the controlled injection system illustrated in FIG. 6 in the second configuration and free of the cavity.

DETAILED DESCRIPTION

The following detailed description and the appended drawings describe and illustrate various exemplary controlled injection devices, systems, and methods. The description and drawings are exemplary in nature and are provided to enable one skilled in the art to make and use one or more exemplary controlled injection devices, controlled injection systems, and/or practice one or more of exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages.

The term "cavity" refers to any space, including, but not limited to, a passageway, blind passageway, body vessel, and/or bodily passage, within any object, including, but not limited to, an object formed of a metal, polymer, bone, and/or tissue. The term "treatment material" refers to any fluid, drug, medication, material, and/or agent used to occupy a cavity, including, but not limited to, bone cement, cells, stem cells, therapeutic agents, and caulk. The term "jig" refers to a device that receives another structure, device, or instrument and controls the location and/or motion of the structure, device, or instrument during use.

Figure 1:
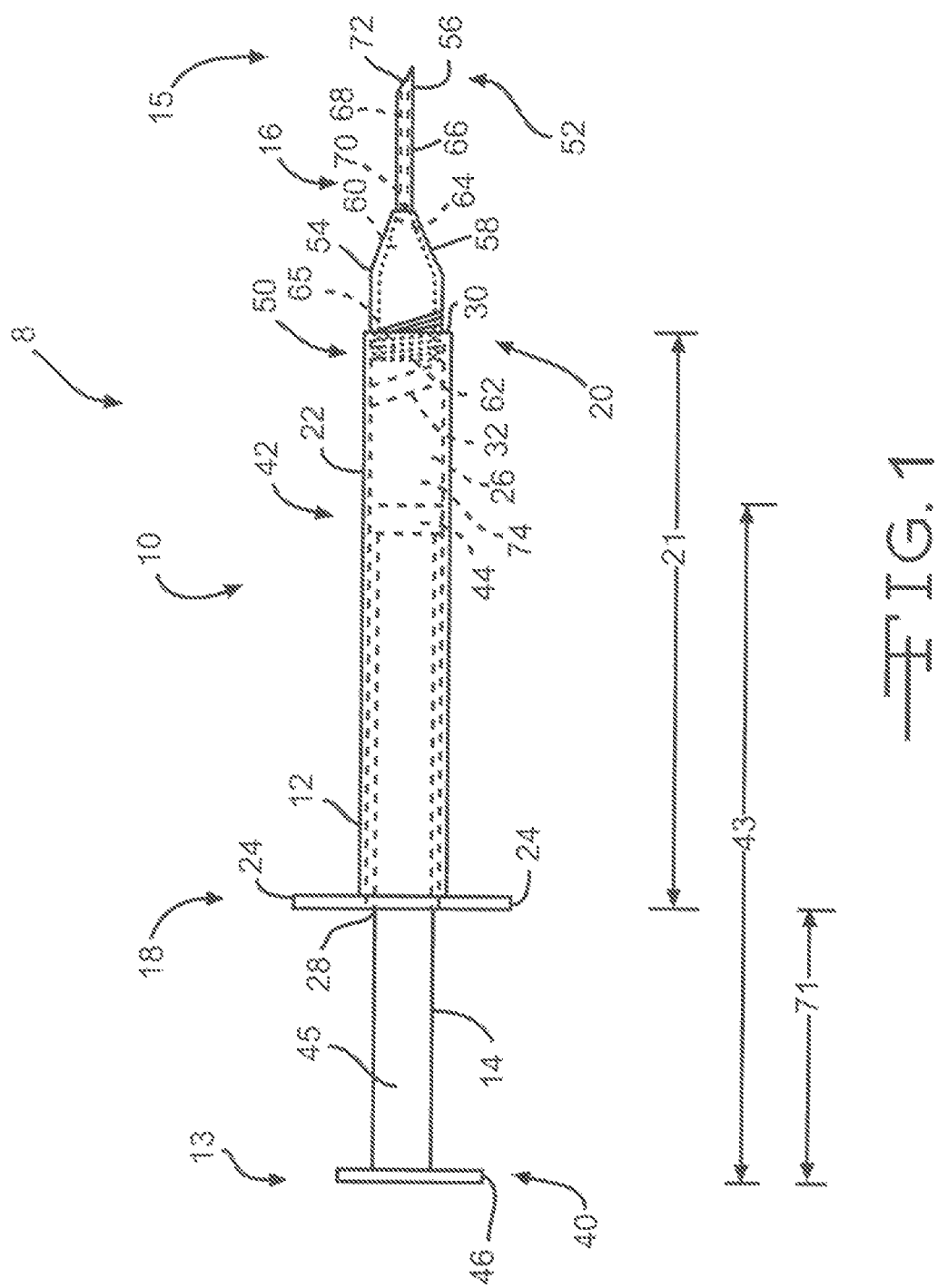
FIG. 1 is a side view of an exemplary injection device in the first configuration.

FIG. 1 illustrates an exemplary injection device 8 adapted to be used in the controlled injection devices, systems, and methods described herein. Any suitable injection device having any suitable structure can be used in a controlled injection device, system, and/or method and skilled artisans will be able to select a suitable injection device and/or structure to include in a controlled injection device, system, and method according to a particular embodiment based on various considerations, including the treatment material desired to be introduced into a cavity. Example injection devices considered suitable include, but are not limited to, devices and/or instruments that are capable of introducing a treatment material into a cavity, devices that include a barrel, plunger and needle, such as syringes, and any other device considered suitable for a particular application.

In the illustrated embodiment, an example of a suitable injection device 8 is syringe 10 that comprises a barrel 12, plunger 14, and needle 16, and has a proximal end 13 and a distal end 15.

Barrel 12 can have any suitable outside diameter and length, and skilled artisans will be able to select a suitable outside diameter and length for a barrel according to a particular embodiment based on various considerations, including the desired amount of treatment material intended to be introduced into a cavity. Barrel 12 can be formed of any suitable material, and skilled artisans will be able to select a suitable material for a barrel according to a particular embodiment based on various considerations, including the type of treatment material being introduced into a cavity. Example materials considered suitable to form a barrel include, but are not limited to, biocompatible materials, materials that can be made biocompatible, glasses, polymers, and any other material considered suitable for a particular application.

In the illustrated embodiment, barrel 12 comprises a barrel proximal end 18, barrel distal end 20, barrel length 21, barrel wall 22, and barrel finger flanges 24. Barrel length 21 extends from barrel proximal end 18 to barrel distal end 20. Barrel wall 22 defines a barrel lumen 26, first barrel opening 28, and second barrel opening 30. Barrel lumen 26 extends from first barrel opening 28 to second barrel opening 30. Each of the barrel finger flanges 24 extends radially outward from barrel wall 22. Barrel distal end 20 defines barrel threads 32 that are adapted to engage with hub threads 65 of needle 16, as described in more detail below. Thus, barrel 12 is adapted to be attached to needle 16.

Optionally, the barrel of an injection device can include one or more indicia along a portion, or the entirety, of the barrel length. The one or more indicia can be formed on the outer surface of barrel, or be embedded within the material forming the barrel. The one or more indicia can be disposed at equal, or varying, lengths from one another along the barrel length and can be used to determine the amount treatment material being stored within the barrel lumen and/or introduced into a cavity. Alternatively, each of the one or more indicia can comprise a raised protuberance extending radially outward from the exterior surface of the barrel. The raised protuberance can extend about the entirety of the circumference, or a portion of the circumference, of the barrel. Any suitable distance can be used to separate each indicium of the one or more indicia from another indicium of the one or more indicia, and skilled artisans will be able to select a suitable distance according to a particular embodiment based on various considerations, including the type of cavity being treated. The distance used to separate each indicium of the one or more indicia from another indicium of the one or more indicia can be measured using any suitable form of measurement. Example forms of measurement considered suitable include, but are not limited to, millimeters, centimeters, and any other form of measurement considered suitable for a particular application.

Plunger 14 can have any suitable outside diameter and length, and skilled artisans will be able to select a suitable outside diameter and length for a plunger according to a particular embodiment based on various considerations, including the structural arrangement of the barrel of an injection device. Plunger 14 can be formed of any suitable material, and skilled artisans will be able to select a suitable material for a plunger according to a particular embodiment based on various considerations, including the type of treatment material being introduced into a cavity. Example materials considered suitable to form a plunger include, but are not limited to, biocompatible materials, materials that can be made biocompatible, glasses, polymers, and any other material considered suitable for a particular application.

In the illustrated embodiment, plunger 14 comprises a plunger proximal end 40, plunger distal end 42, plunger length 43, plunger tip 44, plunger body 45, and plunger finger flange 46. Plunger length 43 extends from plunger proximal end 40 to plunger distal end 42. Plunger tip 44 is attached to plunger distal end 42 and is adapted to be received within barrel lumen 26. Thus, plunger 14 is partially disposed within barrel 12. Plunger finger flange 46 extends radially outward from plunger body 45.

Plunger length 43 is equal to, substantially equal to, greater than, or less than, barrel length 21. It is considered advantageous for plunger length 43 to be equal to, substantially equal to, or greater than, barrel length 21 at least because this configuration advantageously allows for a portion, or the entirety, of a treatment material stored within barrel lumen 26 to pass through needle 16 when barrel distal end 20 is moved towards plunger tip 44, or vice versa.

Plunger 14 is slidably disposed within barrel 12 such that plunger distal end 42 and plunger tip 44 are each moveable within barrel lumen 26 along barrel length 21. Plunger tip 44 is configured to prevent, or substantially prevent, treatment material from passing proximally beyond plunger tip 44 when in use (e.g., disposed within barrel lumen 26). For example, when a treatment material is stored within barrel lumen 26, such as cement, and plunger tip 44 and barrel distal end 20 are moved towards one another, the treatment material within barrel lumen 26 is forced distally through needle 16. This can be accomplished by configuring plunger tip 44 to have an outside diameter that is equal to, substantially equal to, or greater than, the inside diameter of barrel 12. Thus, plunger tip 44 is adapted to provide a moveable sealing engagement with barrel 12.

Needle 16 can have any suitable outside diameter and length, and skilled artisans will be able to select a suitable outside diameter and length for a needle according to a particular embodiment based on various considerations, including the desired amount of treatment material intended to be introduced into a cavity. Needle 16 can be formed of any suitable material, and skilled artisans will be able to select a suitable material for a needle according to a particular embodiment based on various considerations, including the type of treatment material being introduced into a cavity. Example materials considered suitable to form a needle include, but are not limited to, biocompatible materials, materials that can be made biocompatible, metals, polymers, and any other material considered suitable for a particular application.

In the illustrated embodiment needle 16 comprises a needle proximal end 50, needle distal end 52, needle hub 54, and needle shaft 56. Needle hub 54 extends from the needle proximal end 50 towards the needle distal end 52 and has a hub wall 58 that defines a hub lumen 60, hub first opening 62, hub second opening 64, and hub threads 65 at needle proximal end 50. Hub lumen 60 extends from hub first opening 62 to hub second opening 64. Hub threads 65 are adapted to engage with barrel threads 32 to provide a sealing engagement between needle 16 and barrel 12. This advantageously allows for treatment material to be passed between barrel lumen 26, hub lumen 60, and needle shaft 56 (e.g., needle shaft lumen 68). Thus, needle 16 is adapted to be attached to barrel 12.

Needle shaft 56 extends from needle hub 54 to needle distal end 52 and comprises a needle shaft wall 66 that defines a needle shaft lumen 68, needle shaft first opening 70, and needle shaft second opening 72. Needle shaft lumen 68 extends from needle shaft first opening 70 to needle shaft second opening 72. Needle shaft lumen 68 is in fluid communication with hub lumen 60 and barrel lumen 26.

While a threaded connection between barrel 12 and needle 16 has been illustrated and described, any suitable method of attachment between a barrel and needle is considered suitable, and skilled artisans will be able to select a suitable method of attachment between a barrel and a needle according to a particular embodiment based on various considerations, including the treatment material desired to be introduced into a cavity. Example methods of attachment considered suitable between a barrel and a needle include, but are not limited to, threaded connections, fixed connections, integrated components, adhesives, and any other method of attachment considered suitable for a particular application.

Syringe 10 has a first configuration and a second configuration. In the first configuration, plunger tip 44 is disposed proximal to barrel distal end 20 and plunger finger flange 46 is disposed proximal to barrel proximal end 18 a first distance 71 from barrel proximal end 18. In the first configuration, treatment material 74 can be stored in barrel lumen 26. In the second configuration, plunger tip 44 is disposed at, adjacent, or near, barrel distal end 20 and plunger finger flange 46 is disposed proximal to barrel proximal end 18 a second distance (not illustrated) from barrel proximal end 18 that is less than the first distance 71. Thus, when syringe 10 is moved from the first configuration to the second configuration, treatment material 74 that is stored within barrel lumen 26 can be passed through barrel lumen 26, hub lumen 60, and needle shaft lumen 68. FIG. 1 illustrates syringe 10 in the first configuration with treatment material 74 disposed within barrel lumen 26. The inclusion of treatment material is considered optional, as it may be omitted from the syringe or injection devices described herein.

Figure 2:
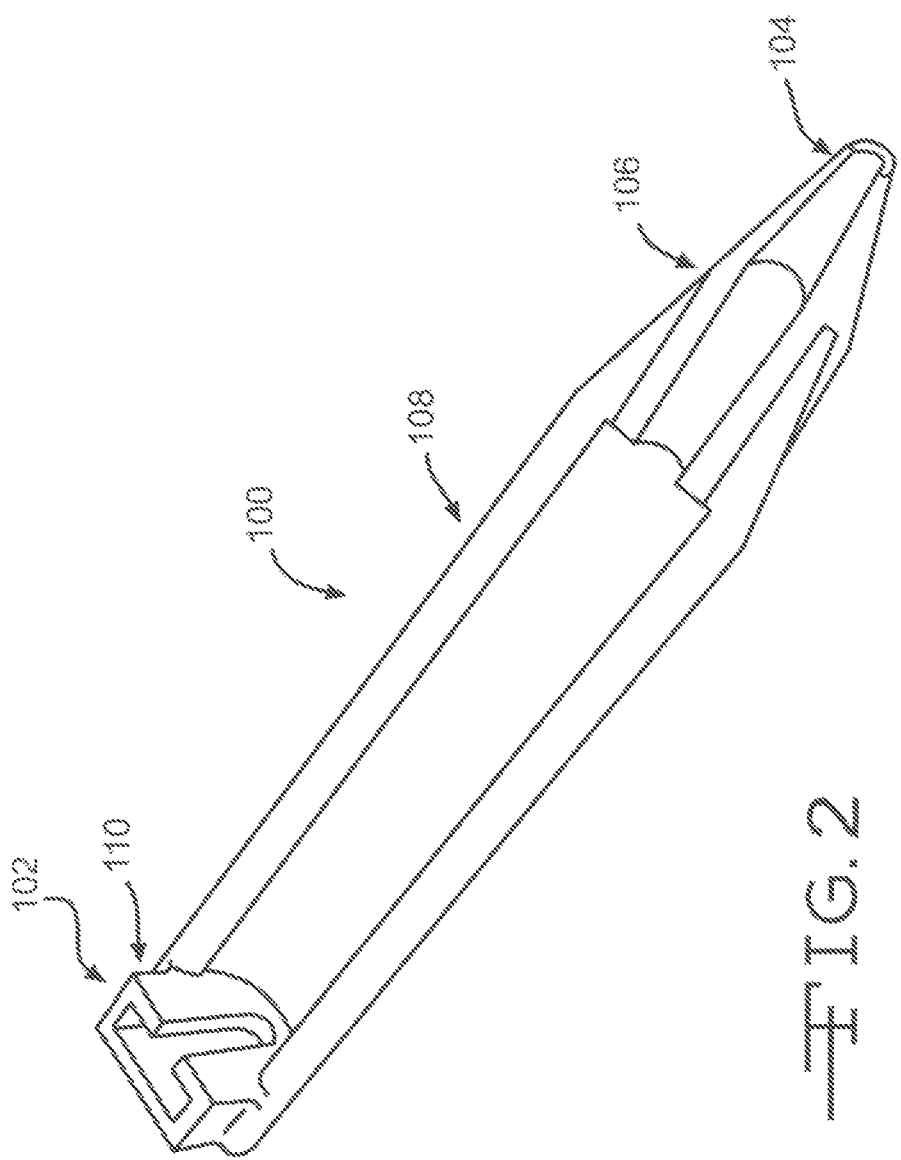
FIG. 2 is a perspective view of an exemplary jig.
Figure 3:
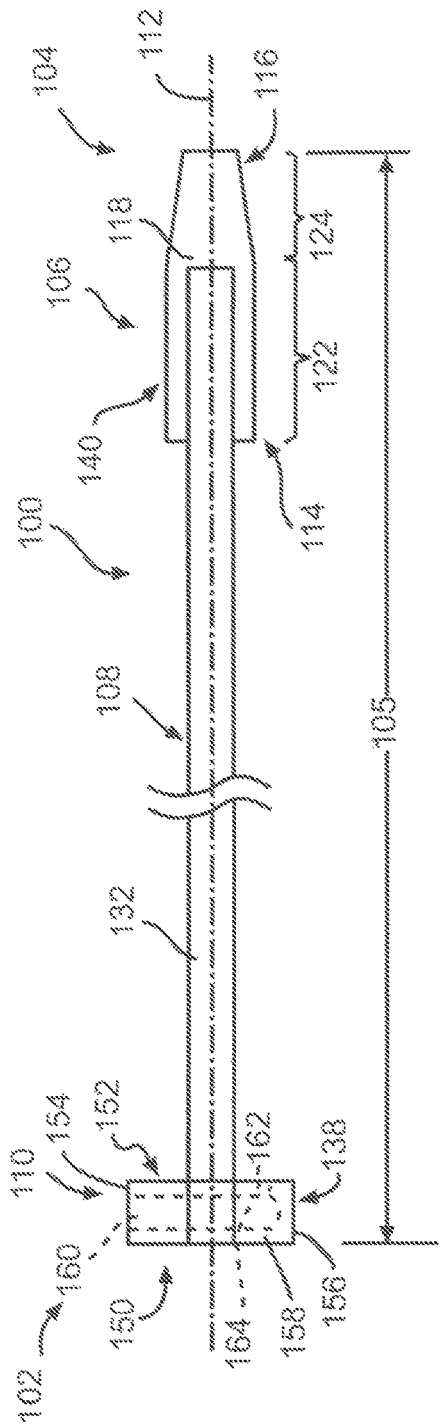
FIG. 3 is a side view of the jig illustrated in FIG. 2.
Figure 4:
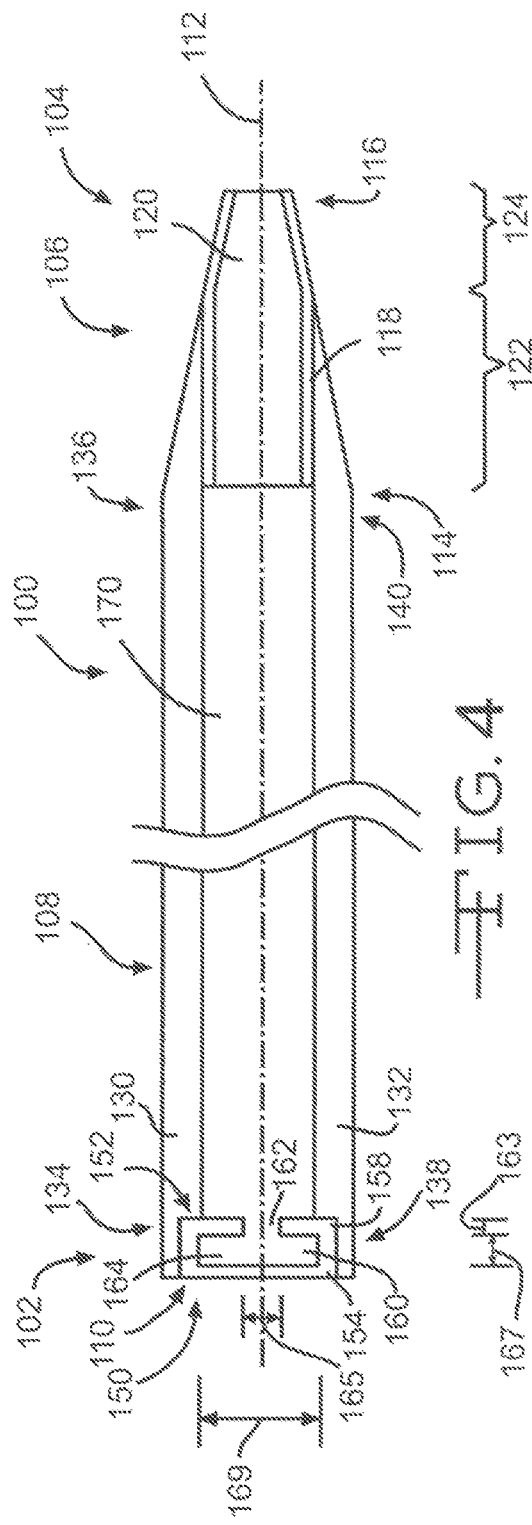
FIG. 4 is a top view of the jig illustrated in FIG. 2.

FIGS. 2, 3, and 4, illustrate an exemplary jig 100 used as a controlled injection device for the introduction of a treatment material into a cavity. In the illustrated embodiment, jig 100 comprises a jig proximal end 102, jig distal end 104, jig length 105, jig head 106, jig shaft 108, jig plunger housing 110, and jig lengthwise axis 112. Jig length 105 extends from jig proximal end 102 to jig distal end 104 and jig lengthwise axis 112 extends through jig length 105.

Jig 100 can have any suitable length, width, and/or structural arrangement, and skilled artisans will be able to select a suitable length, width, and/or structural arrangement for a jig according to a particular embodiment based on various considerations, including the structural arrangement of an injection device intended to be used with the jig. Example structural arrangements considered suitable for a jig include, but are not limited to, jigs that have a jig length that is equal to, substantially equal to, less than, or greater than, the length of an injection device in the first configuration (e.g., 0.5 cc syringe that has treatment material stored in barrel lumen, 1 cc syringe that has treatment material stored in barrel lumen, 1.5 cc syringe that has treatment material stored in barrel lumen), jigs that have a length measured from the plunger housing to the head distal end that is equal to, substantially equal to, less than, or greater than, the length of an injection device in the first configuration (e.g., 0.5 cc syringe that has treatment material stored in barrel lumen, 1 cc syringe that has treatment material stored in barrel lumen, 1.5 cc syringe that has treatment material stored in barrel lumen), and any other structural arrangement considered suitable for a particular application. Various jig structural arrangements are illustrated and described herein. These structural arrangements, however, are not intended to be limiting in nature.

Jig 100 can be formed of any suitable material, and skilled artisans will be able to select a suitable material to form a jig according to a particular embodiment based on various considerations, including the materials forming an injection device intended to be used with the jig. Example materials considered suitable to form a jig include, but are not limited to, biocompatible materials, materials that can be made biocompatible, metals, polymers, high-molecular-weight polymers, thermoplastic materials, polyethylene, polyvinyl chloride, polystyrene, and any other material considered suitable for a particular application.

Jig 100 can be formed using any suitable method, and skilled artisans will be able to select a suitable method to form a jig according to a particular embodiment based on various considerations, including the material(s) that form the jig. Example methods of forming a jig considered suitable include, but are not limited to, injection molding, and any other method of manufacture considered suitable for a particular application.

In the illustrated embodiment, jig head 106 has a head proximal end 114, head distal end 116, and head body 118 that defines head opening 120. The diameter of the outer surface of head body 118 tapers from a location between head proximal end 114 and head distal end 116 to head distal end 116. This structural configuration is considered advantageous at least because it reduces the outer diameter of jig head 106 allowing it to fit into smaller geometries as compared to a jig head that does not taper towards the head distal end. While the diameter of the outer surface of head body 118 has been illustrated and described as tapering from a location between head proximal end 114 and head distal end 116 to head distal end 116, a jig head can have any suitable structural configuration. Skilled artisans will be able to select a suitable structural configuration for a jig head according to a particular embodiment based on various considerations, including the structural arrangement of an injection device intended to be used with the jig. Example structural arrangements considered suitable for a jig head include, but are not limited to, a jig head having a constant, or substantially constant, outer diameter from the jig head proximal end to the jig head distal end, a jig head having an outer diameter that tapers from the jig head proximal end to the jig head distal end, a jig head that has an outer diameter that varies from the jig head proximal end to the jig head distal end, a jig head that tapers from a location between the jig head proximal end and the jig head distal end to the jig head distal end, and any other structural configuration considered suitable for a particular application.

Head opening 120 can comprise any suitable opening, recess, aperture, or other structure capable of receiving a portion, or the entirety, of an injection device (e.g., syringe 10). In the illustrated embodiment, head opening 120 comprises a recess that extends into head body 118 and extends from head proximal end 114 to head distal end 116. Head opening 120 has a head opening first portion 122 that extends from head proximal end 114 towards head distal end 116 and a head opening second portion 124 that extends from head distal end 116 towards head proximal end 114. Head opening first portion 122 has a constant, or substantially constant, diameter and head opening second portion 124 has a diameter that tapers from a location proximal to head distal end 116 to head distal end 116. Thus, head opening 120 has a first diameter at head proximal end 114 and a second, different, diameter at head distal end 116. In the illustrated embodiment, the first diameter at head proximal end 114 is greater than the second diameter at head distal end 116.

Head opening 120 is adapted to receive a portion, or the entirety, of an injection device, such as the barrel of an injection device (e.g., barrel 12), and/or the needle of an injection device (e.g., needle hub 54, needle shaft 56). The structural configuration of jig head 106 is considered advantageous at least because it provides a mechanism for positioning the needle distal end of an injection device at a desired location within a cavity, as described in more detail herein. For example, the tapered configuration of head opening 120 is considered advantageous at least because it provides a mechanism for receiving variously sized injection devices (e.g., 0.5 cc syringe, 1 cc syringe, 1.5 cc syringe).

Head opening 120 can have any suitable structural arrangement and any suitable dimensions, and skilled artisans will be able to select a suitable structural arrangement and dimensions for a head opening of a jig according to a particular embodiment based on various considerations, including the structural arrangement and/or dimensions of an injection device intended to be used with the jig.

While head opening 120 has been illustrated and described as having a first diameter at head proximal end 114 that is greater than a second diameter at head distal end 116, the head opening of a jig can have any suitable diameter at head proximal end and head distal end. Skilled artisans will be able to select a suitable diameter for a head opening according to a particular embodiment based on various considerations, including the structural arrangement of an injection device intended to be used with the jig. Example diameters considered suitable for a head opening include, but are not limited to, a head opening having a first diameter at head proximal end that is greater than, less than, equal to, or substantially equal to, a second diameter at head distal end.

Optionally, one or more protuberances can be attached to head body that extend radially into head opening along a portion, or the entirety, of the length of head opening to provide a mechanism for releasably attaching an injection device to the jig and/or limiting distal advancement of an injection device while disposed within the head opening. The one or more protuberances can be formed of a malleable material, or any other material capable of deforming, and each protuberance can deform while a portion of an injection device is being introduced into a head opening, or while a portion of an injection device is disposed within a head opening. The one or more protuberances can provide a mechanism for releasably attaching a portion of an injection device within a head opening using a snap fit configuration and/or friction fit configuration.

In the illustrated embodiment, jig shaft 108 is attached to jig head 106, extends from jig head 106 towards jig proximal end 102, and comprises a first shaft arm 130 and second shaft arm 132. First shaft arm 130 has a first shaft arm proximal end 134 and a first arm shaft distal end 136 and second shaft arm 132 has a second shaft arm proximal end 138 and a second shaft arm distal end 140. Each of the first shaft arm 130 and second shaft arm 132 extends from jig head 106 to jig plunger housing 110.

While jig shaft 108 has been illustrated and described as having a first shaft arm 130 and a second shaft arm 132, a jig shaft can have any suitable number of shaft arms and/or any suitable structural arrangement. Skilled artisans will be able to select a suitable number of shaft arms and/or structural arrangement for the shaft of a jig according to a particular embodiment based on various considerations, including the structural arrangement of the barrel and/or plunger of an injection device intended to be used with the jig. Example number of shaft arms considered suitable to include in a jig include, but are not limited to, one, at least one, two, a plurality, three, four, five, and any other number considered suitable for a particular application. Alternative to jig shaft having a first shaft arm and a second shaft arm, a jig shaft can have only a first shaft arm or have wall that defines a recess, opening, or notch, that is adapted to receive the barrel and/or barrel finger flange(s) of an injection device.

While each of the first shaft arm 130 and second shaft arm 132 has been illustrated and described as extending from jig head 106 to jig plunger housing 110, a jig shaft can extend any suitable distance along a jig length, and skilled artisans will be able to select a suitable distance for a jig shaft to extend along a jig length according to a particular embodiment based on various considerations, including the structural arrangement of an injection device intended to be used with a jig. Example distances considered suitable for a jig shaft to extend along a jig length include, but are not limited to, a jig shaft that extends from a jig proximal end to a jig distal end, a jig shaft that extends from a location between a head proximal end and a head distal end to a jig proximal end, a jig shaft that extends from a head distal end to a jig proximal end, a jig shaft that extends from a location between a plunger housing proximal end and a plunger housing distal end to a head proximal end, a jig shaft that extends from a location between a plunger housing proximal end and a plunger housing distal end to a location between a head proximal end and a head distal end, a jig shaft that extends from a location between a plunger housing proximal end and a plunger housing distal end to a head distal end, a jig shaft that extends from a plunger housing distal end to a head proximal end, a jig shaft that extends from a plunger housing distal end to a location between a head proximal end and a head distal end, a jig shaft that extends from a plunger housing distal end to a head distal end, and any other structural configuration considered suitable for a particular application.

While jig shaft 108 has been illustrated and described as attached to jig head 106, any suitable type of attachment can be used between a jig head and a jig shaft, and skilled artisans will be able to select a suitable type of attachment between a jig head and a jig shaft according to a particular embodiment based on various considerations, including the materials that form the jig head and/or jig shaft. Example forms of attachment considered suitable between a jig head and a jig shaft include, but are not limited to, fixed attachment, releasable attachment, an integrated association between the jig head and the jig shaft, attaching the jig head such that it is moveable along the length of the jig shaft, and any other form of attachment considered suitable for a particular application.

In the illustrated embodiment, jig plunger housing 110 is disposed on jig shaft 108 and comprises a plunger housing proximal end 150, plunger housing distal end 152, plunger housing first surface 154, plunger housing second surface 156, and a plunger housing body 158. Jig plunger housing 110 has a length that is disposed orthogonal, or substantially orthogonal, to jig lengthwise axis 112. Plunger housing first surface 154 is opposably facing, or substantially opposably facing, plunger housing second surface 156. Plunger housing first surface 154 is disposed orthogonal, or substantially orthogonal, to plunger housing distal end 152.

Plunger housing body 158 defines a plunger housing recess 160 that extends into jig plunger housing 110 from plunger housing first surface 154 and towards plunger housing second surface 156. Plunger housing recess 160 is adapted to receive a portion, or the entirety, of the plunger of an injection device (e.g., plunger proximal end 40, plunger body 45, plunger finger flange 46). Plunger housing recess 160 has a plunger housing recess first portion 162 and a plunger housing recess second portion 164. Plunger housing recess first portion 162 extends from plunger housing distal end 152 towards plunger housing proximal end 150. Plunger housing recess first portion 162 extends into jig plunger housing 110 a plunger housing first recess length 163 measured along jig length 105 and has a plunger housing first recess width 165 measured along plunger housing distal end 152. Plunger housing recess second portion 164 extends from plunger housing recess first portion 162 and towards plunger housing proximal end 150. Plunger housing recess second portion 164 extends into jig plunger housing 110 a plunger housing second recess length 167 measured along jig length 105 and has a plunger housing second recess width 169 measured along plunger housing distal end 152.

In the illustrated embodiment, plunger housing first recess length 163 is less than plunger housing second recess length 167 and plunger housing first recess width 165 is less than plunger housing second recess width 169. This configuration is considered advantageous at least because it provides a mechanism for receiving and releasably attaching a portion of the plunger of an injection device (e.g., plunger proximal end 40, plunger body 45, plunger finger flange 46) to jig 100 and maintaining the axial position of the plunger of the injection device relative to the jig 100.

While a particular structural arrangement has been described and illustrated for jig plunger housing 110, the jig plunger housing of a jig can have any suitable structural arrangement. Skilled artisans will be able to select a suitable structural arrangement for a jig plunger housing according to a particular embodiment based on various considerations, including the structural arrangement of the plunger of an injection device. For example, alternative to plunger housing first recess length 163 being less than plunger housing second recess length 167, as illustrated and described above, a plunger housing first recess length can be equal to, substantially equal to, or greater than, a plunger housing second recess length. In addition, alternative to plunger housing first recess width 165 being less than plunger housing second recess width 169, as illustrated and described above, a plunger housing first recess width can be equal to, substantially equal to, or greater than, a plunger housing second recess width. In this configuration, a protuberance can extend radially inward from plunger housing wall and into the plunger housing recess between the plunger housing recess first portion and the plunger housing recess second portion to prevent, or substantially prevent, axial movement of the plunger when disposed in the plunger housing recess. The protuberance can be a separate element attached to the jig plunger housing or be integral with the jig plunger housing.

Jig head 106, jig shaft 108, and jig plunger housing 110 define a jig opening 170 that extends along the jig length 105 between jig proximal end 102 and jig distal end 104. It is considered advantageous to include a jig opening 170 at least because it allows each of the barrel finger flanges of an injection device (e.g., barrel finger flanges 24) to extend radially outward from jig lengthwise axis 112 and allows for movement of the barrel of an injection device along jig length 105 while the plunger of the injection device is fixed, or releasably fixed, to jig plunger housing 110.

Figure 5:
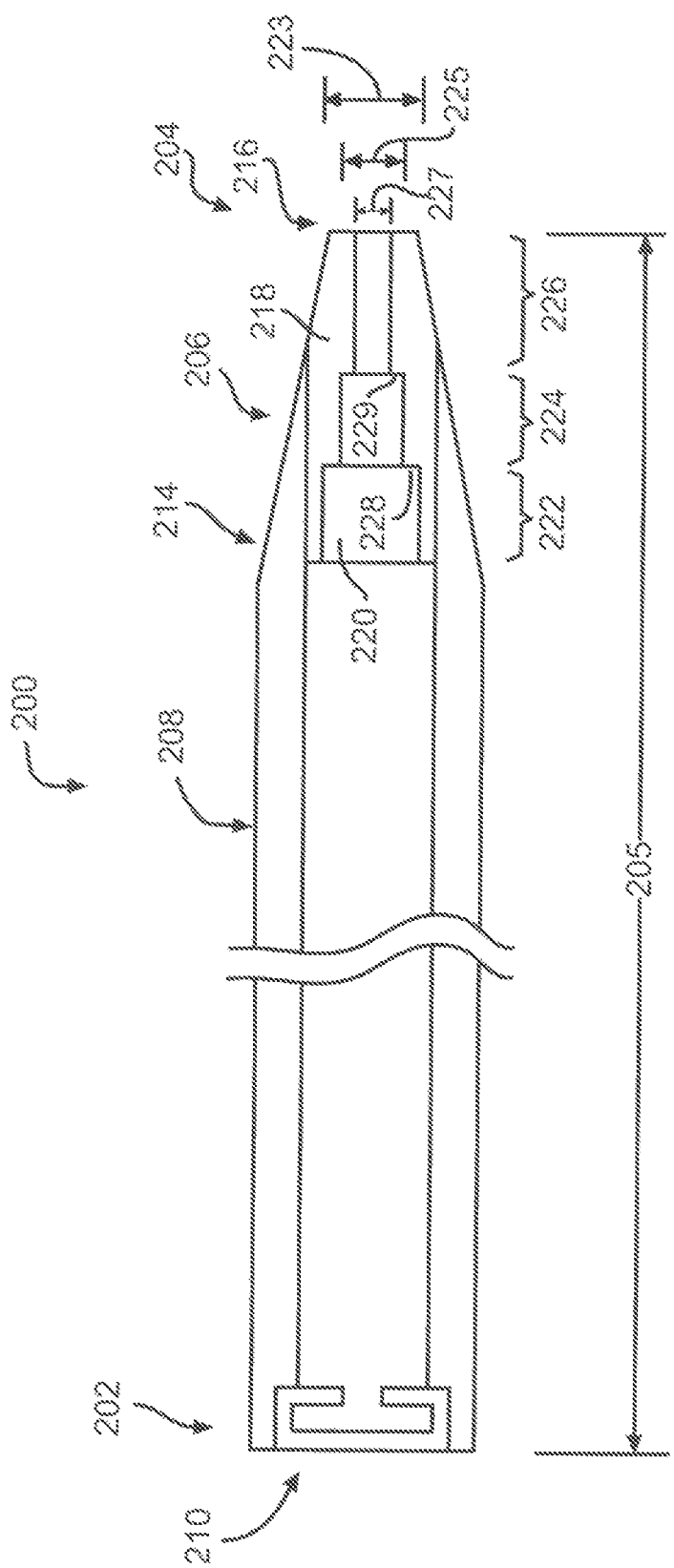
FIG. 5 is a top view of a first alternative jig.

FIG. 5 illustrates a first alternative jig 200. Jig 200 is similar to jig 100 illustrated in FIGS. 2, 3, and 4, and described above, except as detailed below. Reference numbers in FIG. 5 refer to the same structural element or feature referenced by the same number in FIGS. 2, 3, and 4, offset by 100. Thus, jig 200 comprises a jig proximal end 202, jig distal end 204, jig length 205, jig head 206, jig shaft 208, and a jig plunger housing 210.

In the illustrated embodiment, head body 218 defines a head opening 220 that has a head opening first portion 222, head opening second portion 224, and a head opening third portion 226. Head opening first portion 222 extends from head proximal end 214 towards head distal end 216, head opening second portion 224 is disposed between head proximal end 214 and head distal end 216, and head opening third portion 226 extends from head distal end 216 towards head proximal end 214.

Head opening first portion 222 has a first diameter 223, head opening second portion 224 has a second diameter 225, and head opening third portion 226 has a third diameter 227. First diameter 223 is different than the second diameter 225 and second diameter 225 is different than the third diameter 227. In the illustrated embodiment, first diameter 223 is greater than second diameter 225 and second diameter 225 is greater than third diameter 227. This configuration advantageously defines a first shoulder 228 between head opening first portion 222 and head opening second portion 224 and a second shoulder 229 between head opening second portion 224 and head opening third portion 226.

It is considered advantageous for head body 218 to define head opening first portion 222, head opening second portion 224, and head opening third portion 226 at least because this structural configuration allows for injection devices having different barrel diameters and/or lengths to be used with jig 200. In addition, it is considered advantageous for head body 218 to define first shoulder 228 and second shoulder 229 at least because each of the shoulders provides a mechanical stop to distal movement of the barrel of an injection device when it is disposed within head opening 220.

While head body 218 has been illustrated and described as defining head opening first portion 222, head opening second portion 224, and head opening third portion 226, the head body of a jig head can define any suitable number of head opening portions having any suitable diameter. Skilled artisans will be able to select a suitable number of head opening portions and a suitable diameter for each head opening portion to include in a jig according to a particular embodiment based on various considerations, including the number and/or size of the injection device(s) intended to be used with the jig. Example numbers of head opening portions considered suitable to include in a jig include, but are not limited to, one, at least one, two, a plurality, three, four, five, six, and any other number considered suitable for a particular application. Example diameters considered suitable for a head opening portion include, but are not limited to, the outer diameter of a desired needle hub of an injection device (e.g., 0.5 cc syringe, 1 cc syringe, 1.5 cc syringe), the outer diameter of a desired barrel of an injection device (e.g., 0.5 cc syringe, 1 cc syringe, 1.5 cc syringe), and any other diameter considered suitable for a particular application.

Figure 6:
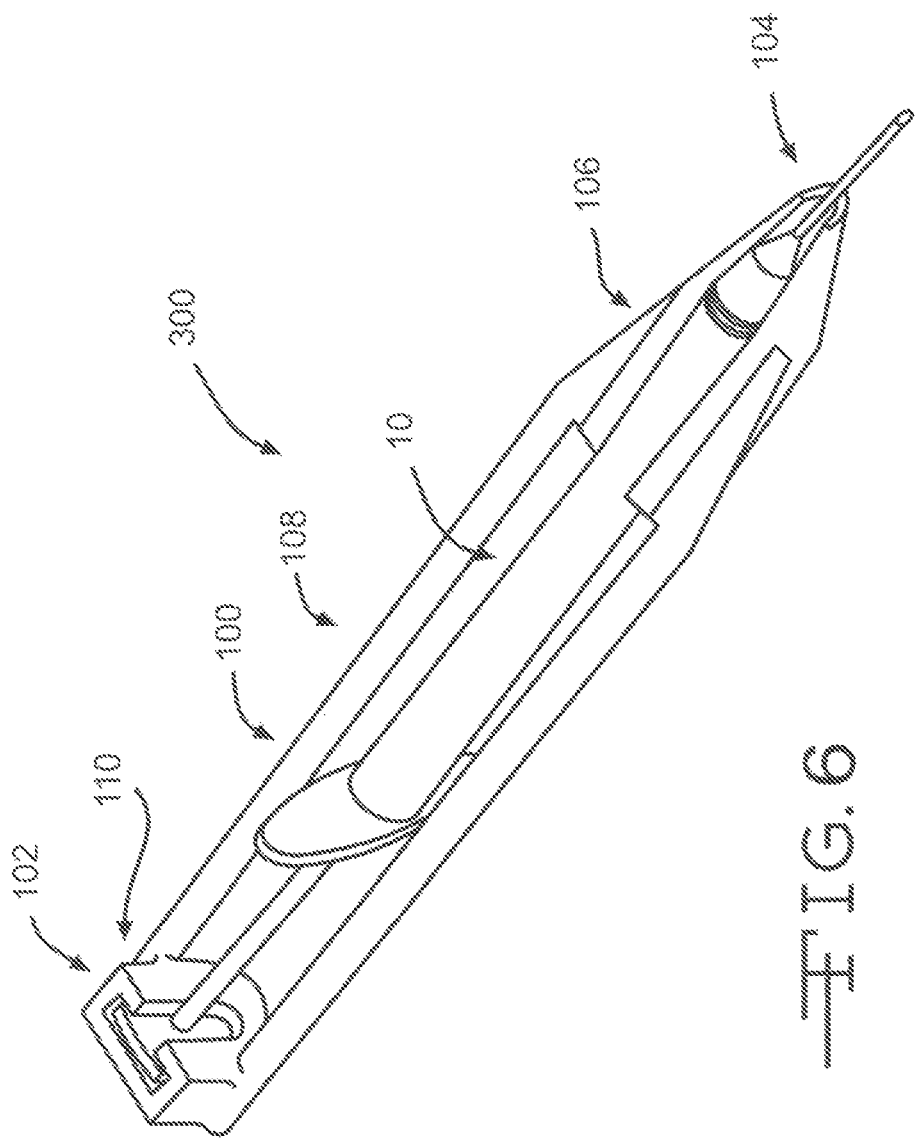
FIG. 6 is a perspective view of an exemplary controlled injection system in the first configuration.

FIGS. 6, 7, 8, and 9, illustrate an exemplary controlled injection system 300 comprising the exemplary syringe 10 illustrated in FIG. 1 disposed within the exemplary jig 100 illustrated in FIGS. 2, 3, and 4. Reference numbers in FIGS. 6, 7, 8, and 9, refer to the same structural element or feature referenced by the same number in FIGS. 1, 2, 3, and 4. Thus, syringe 10 comprises a barrel 12, plunger 14, and needle 16 and jig 100 comprises a jig head 106, jig shaft 108, and a jig plunger housing 110. FIGS. 6, 7, and 8, illustrate the controlled injection system 300 in the first configuration and FIG. 9 illustrates the controlled injection system 300 in the second configuration.

In the illustrated embodiment, plunger finger flange 46 is disposed within plunger housing recess 160 such that plunger 14 is fixed relative to jig 100. Thus, plunger 14 is prevented, or substantially prevented, from moving axially along jig length 105. Each of barrel distal end 20 and needle hub 54 is disposed within head opening 120 and needle distal end 52 is disposed distal to jig distal end 104. Barrel finger flanges 24 are disposed within, and extend radially outward of, jig opening 170 and are adapted to move axially within jig opening 170 along jig length 105. Thus, barrel 12 is adapted to move axially along jig length 105.

In the first configuration, as illustrated in FIGS. 6, 7, and 8, syringe 10 is disposed within jig 100 such that barrel distal end 20 and/or needle hub 54 contacts head body 118 preventing, or substantially preventing, barrel 12 from moving distally along jig length 105. Barrel distal end 20 and/or needle hub 54 contacts head body 118 at a point where the taper of head opening second portion 124 defines a diameter that is equal to, substantially equal to, or less than, the diameter of barrel 12 and/or needle hub 54. This configuration is considered advantageous at least because it positions needle distal end 52 distal to jig distal end 104 and allows proximal movement of barrel 12 within jig 100 along jig length 105. For example, barrel 12 and needle 16 are able to move towards jig proximal end 102. It is considered advantageous for the barrel distal end 20 and/or needle hub 54 to contact the wall of head body 118 within head opening 120 at least because this configuration prevents needle distal end 52 from extending beyond a desired distance from jig distal end 104. The taper defined along the length of head opening second portion 124 advantageously allows for a number of differently sized barrels and/or needle hubs to be utilized within jig 100.

In the first configuration, plunger tip 44 is disposed proximal to barrel distal end 20, plunger finger flange 46 is disposed proximal to barrel proximal end 18 a first distance 171, and treatment material 74 is stored in barrel lumen 26. In addition, barrel distal end 20 and/or needle hub 54 is contacting, or interacting with, head body 118 and needle distal end 52 is disposed distal to jig distal end 104. By placing a proximal force on barrel 12 (e.g., barrel finger flanges 24) in the direction of arrow 172, syringe 10 can be moved to the second configuration, as shown in FIG. 9, and treatment material 74 can be passed through barrel lumen 26 and needle shaft lumen 68.

In the second configuration, plunger tip 44 is disposed at, or near, barrel distal end 20, plunger finger flange 46 is disposed proximal to barrel proximal end 18 a second distance 173 from barrel proximal end 18 that is less than the first distance 171, and a portion, or the entirety, of treatment material 74 has been expelled from barrel lumen 26. Thus, when syringe 10 is moved from the first configuration to the second configuration, treatment material 74 that is stored within barrel lumen 26 is passed through barrel lumen 26, hub lumen 60, and needle shaft lumen 68. In addition, in the second configuration, each of the barrel distal end 20 and/or needle hub 54 has been withdrawn proximally within head opening 120 such that needle distal end 52 has been advanced proximally and is positioned at, or near, jig distal end 104.

While barrel distal end 20 and/or needle hub 54 have been illustrated and described as interacting with, or contacting, jig head 106 (e.g., head body 118), any suitable portion of an injection device can contact a jig to prevent, or substantially prevent, distal axial movement of the injection device. The portion of an injection device contacting, or interacting with, a jig will depend on the structural arrangement of the injection device. As described herein, any suitable injection device, having any suitable structural arrangement, can be used in combination with the jigs described herein. Skilled artisans will be able to select a suitable injection device to use with a jig according to a particular embodiment based on various considerations, including the amount of treatment material desired to be introduced into a cavity. For example, a portion, or the entirety, of a barrel, needle hub, and any other portion of an injection device, can interact, or contact, a jig head.

While needle distal end 52 has been illustrated and described as positioned at, or near, jig distal end 104 when controlled injection system 300 and/or syringe 10 is in the second configuration, the needle distal end of a syringe can be positioned at any suitable location along a jig length, or beyond a jig length, when a controlled injection system and/or syringe is the first configuration or second configuration. Skilled artisans will be able to select a suitable position for a needle distal end with respect to a controlled injection system according to a particular embodiment based on various considerations, including the depth of a cavity that is being treated. Example positions considered suitable for a needle distal end of an injection device when a controlled injection system and/or syringe is in the first configuration or second configuration include, but are not limited to, distal to a jig distal end, at a jig distal end, near a jig distal end, and proximal to a jig distal end.

FIG. 10 illustrates the exemplary controlled injection system 300 illustrated in FIGS. 6, 7, 8, and 9 partially disposed within a cavity 302. FIG. 11 illustrates the exemplary controlled injection system 300 illustrated in FIGS. 6, 7, 8, and 9, free of the cavity 302. Reference numbers in FIGS. 10 and 11 refer to the same structural element or feature referenced by the same number in FIGS. 6, 7, 8, and 9. Thus, syringe 10 comprises a barrel 12, plunger 14, and needle 16 and jig 100 comprises a jig head 106, jig shaft 108, and a jig plunger housing 110. FIG. 10 illustrates controlled injection system 300 in the first configuration and FIG. 11 illustrates controlled injection system 300 in the second configuration.

FIGS. 10 and 11 illustrate a cavity 302 formed in bone 304. The cavity 302 comprises a cavity opening 306 and a cavity distal end 308. When it is desired to introduce a treatment material 74 (e.g., cement) into cavity 302, syringe 10 is loaded within jig 100, as described herein, such that barrel distal end 20 and/or needle hub 54 contacts head body 118 and needle distal end 52 is disposed distal to jig distal end 104. As illustrated in FIG. 10, needle distal end 52 is advanced into cavity 302 until jig distal end 104 contacts bone 304. The interaction of bone 304 and jig distal end 104 acts as a mechanical stop preventing distal advancement of jig 100 beyond where jig distal end 104 contacts bone 304.

Thus, controlled injection system 300 provides a mechanism for advancing a needle distal end 52 into a cavity 302 a predetermined distance. The distance a needle 16 is advanced into a cavity 302 is based on the structural configuration of jig 100 (e.g., jig head 106, jig shaft 108, jig plunger housing 110) and/or the structural arrangement of the injection device being used.

As illustrated in FIG. 11, when barrel 12 is moved proximally along jig length 105 in the direction of arrow 172, needle distal end 52 is withdrawn proximally out of cavity 302 through cavity opening 306 and treatment material 74 is introduced into cavity 302. Thus, movement of syringe 10 from the first configuration to the second configuration passes treatment material 74 stored within barrel lumen 26 through hub lumen 60 and needle shaft lumen 68. Depending on the length of the barrel 12 and/or needle 16, when controlled injection system 300 and/or syringe 10 are in the second position, needle distal end 52 can be free of cavity 302 or disposed within cavity 302.

The configuration of jig 100 is considered advantageous at least because it allows for treatment material 74 stored within barrel lumen 26 to be introduced into cavity 302 continuously, or substantially continuously, while simultaneously withdrawing needle distal end 52 from cavity 302. This prevents, or substantially prevents, disruption in treatment material 74 as it is being introduced into cavity 302. The configuration of jig 100 is also considered advantageous at least because it provides a mechanism for controlling the placement of treatment material 74 within a cavity. For example, some cavities can have a distal end formed of a soft tissue for which it is not desired to introduce treatment material. The configuration of jig 100 provides a mechanical stop to distal advancement of a needle distal end within a cavity such that treatment material can be positioned within the cavity at a desired point of treatment as the barrel of an injection device is advanced proximally.

Needle distal end 52 can be positioned at any suitable distance from jig distal end 104 when injection device 10 is in the first configuration, and skilled artisans will be able to select a suitable distance to position a needle distal end from a jig distal end according to a particular embodiment based on various considerations, including the location of the cavity. For example, a needle distal end can be positioned a distance from a jig distal end that is based on one or more attributes, such as the cavity depth, cavity volume, needle length, barrel length, plunger length, injection device length in the first configuration, injection device length in the second configuration, jig length, jig head length, jig shaft length, jig plunger housing length, and any other attribute considered suitable for a particular application. Example methods of positioning a needle distal end a distance from a jig distal end are described herein.

While a cavity 302 has been illustrated and described as formed in bone 304, the jigs and/or controlled injection devices described herein can be used to treat a cavity formed in any material and/or portion of a body, and skilled artisans will be able to select a suitable cavity to treat using one of the jigs and/or controlled injection devices described herein according to a particular embodiment based on various considerations, including the treatment material desired to be introduced into the cavity. Example uses for the jigs and/or controlled injection devices described herein include, but are not limited to, cell therapy (e.g., stem cell therapy), repeated injections of a treatment material, and any other use considered suitable for a particular application. For example, the jigs and/or controlled injection devices described herein can be utilized to introduce stem cells into a cavity.

Figure 12:
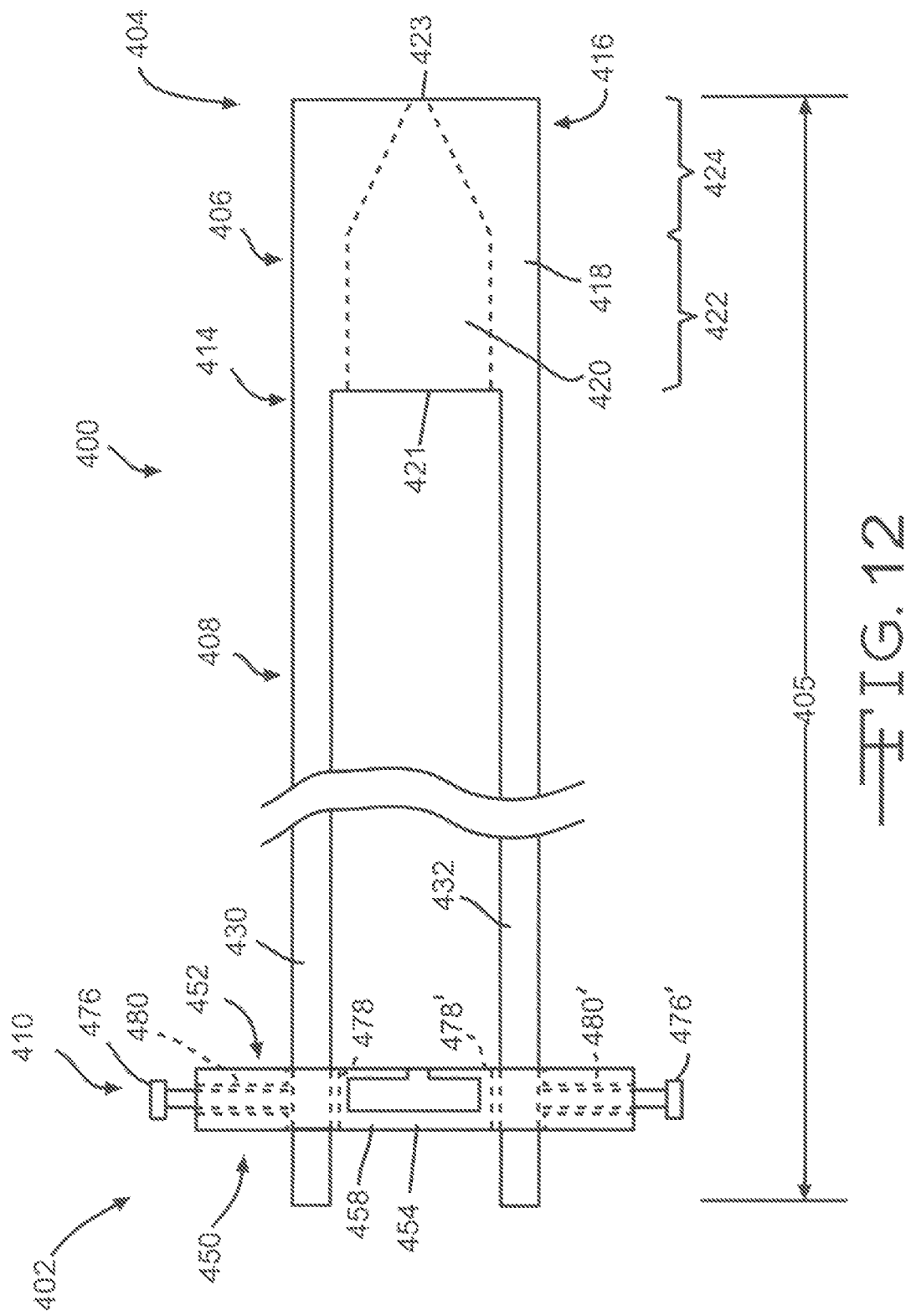
FIG. 12 is a top view of a second alternative jig.

FIG. 12 illustrates a second alternative jig 400. Jig 400 is similar to jig 100 illustrated in FIGS. 2, 3, and 4, and described above, except as detailed below. Reference numbers in FIG. 12 refer to the same structural element or feature referenced by the same number in FIGS. 2, 3, and 4, offset by 300. Thus, jig 400 comprises a jig proximal end 402, jig distal end 404, jig head 406, jig shaft 408, and jig plunger housing 410.

In the illustrated embodiment, jig head body 418 defines a head opening 420 that extends from a head first opening 421 on head proximal end 414 to a head second opening 423 on the head distal end 416. Thus, jig opening 420 comprises a head aperture that extends into head body 418 and extends from head proximal end 414 to head distal end 416. Head opening 420 has a head opening first portion 422 that extends from head first opening 421 towards head distal end 416 and a head opening second portion 424 that extends from head second opening 423 towards head proximal end 414. Head opening first portion 422 has a constant, or substantially constant, diameter and head opening second portion 424 has a diameter that tapers from a location proximal to head distal end 416 to head distal end 416. Thus, head opening 420 has a first diameter at head proximal end 414 and a second, different, diameter at head distal end 416. In the illustrated embodiment, the first diameter at head proximal end 414 is greater than the second diameter at head distal end 416.

In the illustrated embodiment, jig plunger housing 410 is adjustable along jig length 405 on jig shaft 408 and comprises a plunger housing proximal end 450, plunger housing distal end 452, plunger housing first surface 454, plunger housing second surface (not shown), plunger housing body 458, and plunger housing fasteners 476, 476'. Thus, jig plunger housing 410 is adapted to move axially along jig length 405 on jig shaft 408 and between a first position along jig length 405 to a second position along jig length 405 that is different than the first position. Plunger housing body 458 defines a first plunger housing aperture 478, second plunger housing aperture 478', third plunger housing aperture 480, and a fourth plunger housing aperture 480'. Each of the third plunger housing aperture 480 and fourth plunger housing aperture 480' is threaded along a portion, or the entirety, of its length.

First plunger housing aperture 478 extends from a first opening on plunger housing proximal end 450 to a second opening on plunger housing distal end 452. Second plunger housing aperture 478' extends from a first opening on plunger housing proximal end 450 to a second opening on plunger housing distal end 452. First plunger housing aperture 478 is adapted to receive a portion of first shaft arm 430 and second plunger housing aperture 478' is adapted to receive a portion of second shaft arm 432.

Third plunger housing aperture 480 extends from a first opening disposed between plunger housing proximal end 450 and plunger housing distal end 452 to a second opening disposed between plunger housing proximal end 450 and plunger housing distal end 452 and in communication with first plunger housing aperture 478. Fourth plunger housing aperture 480' extends from a first opening disposed between plunger housing proximal end 450 and plunger housing distal end 452 to a second opening disposed between plunger housing proximal end 450 and plunger housing distal end 452 and in communication with second plunger housing aperture 478'. Thus, third plunger housing aperture 480 is in communication with first plunger housing aperture 478 and fourth plunger housing aperture 480' is in communication with second plunger housing aperture 478'. Third plunger housing aperture 480 is adapted to receive a portion, or the entirety, of plunger housing fastener 476 and fourth plunger housing aperture 480' is adapted to receive a portion, or the entirety, of a plunger housing fastener 476'.

Each of the plunger housing fasteners 476, 476' is threaded along a portion, or the entirety, of its length and is adapted to be received by its respective plunger housing aperture 480, 480'. Each of the plunger housing fasteners 476, 476' has a first configuration and a second configuration. In the first configuration, each of the plunger housing fasteners 476, 476' is free, or substantially free, of jig shaft 408. In the second configuration, each of the plunger housing fasteners 476, 476' is in contact with, or substantially contacting, jig shaft 408 to prevent, or substantially prevent, axial movement of jig head housing 410 along jig length 405. Thus, plunger housing fasteners 478, 478' are adapted to releasably attach jig plunger housing 410 to jig shaft 408 and jig plunger housing 410 is slidable along jig length 405 on jig shaft 408. This configuration is considered advantageous at least because it provides a mechanism for customizing jig 400 to receive a variety of barrel lengths and/or needle lengths. In addition, this configuration is considered advantageous at least because it provides a mechanism for positioning the needle distal end at a predetermined distance from jig distal end 404.

While plunger housing head fasteners 476, 476' have been illustrated and described as providing a mechanism for preventing, or substantially preventing, axial movement of jig head housing 410 along jig length 405, any suitable structure capable of providing a mechanism to adjust the position of a jig head housing along a jig length can be used. Skilled artisans will be able to select a suitable structure to include with a jig to adjust the position of a jig head housing according to a particular embodiment based on various considerations, including the materials forming the jig. Example structure considered suitable to provide a mechanism to adjust the position of a jig head housing along a jig length include, but are not limited to, a ratcheting system, spring loaded lock and release system (e.g., ball bearing mechanism), using a retaining pin disposed through a lumen defined by the jig head housing, a collet, a screw type collet, and any other structure considered suitable for a particular application.

While a third plunger housing aperture 480, fourth plunger housing aperture 480', and two plunger housing fasteners 476, 476' have been illustrated and described, any suitable number of apertures can be defined by a plunger housing body and any suitable number of fasteners can be used to releasably attach a plunger housing along a jig length. Skilled artisans will be able to select a suitable number of apertures for a plunger housing body to define and a suitable number of fasteners to include with a jig to achieve releasable attachment between a jig plunger housing and a jig shaft according to a particular embodiment based on various considerations, including the structural arrangement of the jig. Example number of apertures considered suitable for a plunger housing body to define include, but are not limited to, one, at least one, two, a plurality, three, four, and any other number considered suitable for a particular application. Example number of plunger housing fasteners considered suitable to include with a jig include, but are not limited to, one, at least one, two, a plurality, three, four, and any other number considered suitable for a particular application.

Various methods of introducing a treatment material into a cavity having a cavity wall are provided. While the methods described herein are shown and described as a series of acts, it is to be understood and appreciated that the methods are not limited by the order of acts, as some acts may, in accordance with these methods, occur in different orders, and/or concurrently with other acts described herein.

Figure 13:
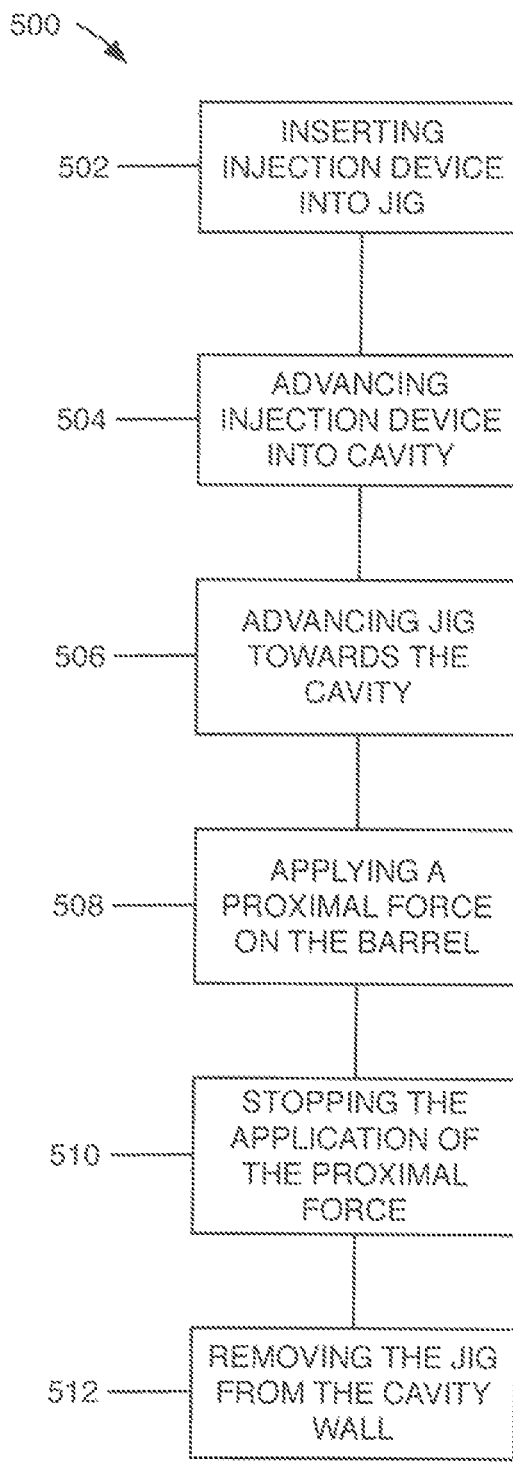
FIG. 13 is a flowchart representation of an exemplary method of introducing a treatment material into a cavity.

FIG. 13 is a flowchart representation of an exemplary method 500 of introducing a treatment material into a cavity having a cavity wall.

A step 502 comprises inserting an injection device (e.g., syringe 10) having an injection device proximal end, an injection device distal end, a barrel, a plunger, and a needle into a jig having a jig proximal end and a jig distal end such that the injection device distal end is disposed distal to the jig distal end and the plunger is fixed relative to the jig. The barrel containing a treatment material. Another step 504 comprises advancing the injection device distal end into a cavity. Another step 506 comprises advancing the jig towards the cavity wall such that it contacts the cavity wall. Another step 508 comprises applying a proximal force on the barrel such that the barrel moves proximally with respect to the jig, injection device distal end is withdrawn in the cavity in a proximal direction, and the treatment material is introduced into the cavity. Another step 510 comprises stopping the application of the proximal force on the barrel. Another step 512 comprises removing the jig from the cavity wall.

Step 502 can be accomplished using any suitable injection device and/or jig. Skilled artisans will be able to select a suitable injection device and/or jig to include in the methods described herein according to a particular embodiment based on various considerations, including the type of treatment material desired to be introduced into a cavity. Example injection devices considered suitable to accomplish the methods described herein include, but are not limited to, injection device 8, and any other injection device considered suitable for a particular application. Example jigs considered suitable to accomplish the methods described herein include, but are not limited to, jig 100, jig 200, jig 400, jig 800, and any other jig considered suitable for a particular application.

Step 502 can be accomplished by inserting the plunger proximal end of an injection device (e.g., plunger proximal end 40) within a jig plunger housing (e.g., jig plunger housing 110) and the barrel distal end (e.g., barrel distal end 20) and/or needle hub (e.g., needle hub 54) within a head opening of a jig (e.g., head opening 120).

An optional step comprises determining the location and size of the cavity, or the portion of the cavity, within which it is desired to introduce treatment material. This step can be accomplished by locating the cavity using direct visualization, or other visualization techniques (e.g., scope), and measuring the cavity, or portion thereof, for which it is desired to introduce treatment material. Another optional step comprises determining the amount of treatment material desired to be introduced into a cavity, or portion of a cavity. This step can be accomplished using any suitable method. For example, this step can be accomplished using the information gathered from the step of determining the location and size of the cavity, or the portion of the cavity, within which it is desired to introduce treatment material. Another optional step is determining the size of an injection device to insert into a jig.

For example, an optional step comprises measuring the cavity depth, cavity diameter, and/or cavity volume. Another optional step comprises selecting an injection device that has a barrel lumen diameter that is complementary to the cavity diameter. Another optional step comprises inserting the injection device having an injection device proximal end, an injection device distal end, a barrel, a needle, and a plunger containing no treatment material in the barrel into a jig having a jig proximal end and a jig distal end such that the injection device distal end is disposed distal to the jig distal end and the injection device proximal end is fixed relative to the jig. Another optional step comprises positioning the injection device distal end (e.g., needle distal end) distal to the jig distal end a distance equal to, or substantially equal to, greater than, or less than, the measurement obtained in the step of measuring the cavity depth. Another optional step comprises recording the plunger distal end position within the barrel while the injection device distal end is disposed distal to the jig distal end. Another optional step comprises removing the injection device from the jig. Another optional step comprises depressing the plunger such that the plunger distal end is disposed at, adjacent, or near, the barrel distal end. Another optional step comprises introducing treatment material into the barrel such that the plunger distal end is disposed at, or near, the positioned within the barrel obtained in the step of recording the plunger distal end position within the barrel.

Another optional step that can be completed prior to, in combination with, or subsequent to, step 502 comprises adjusting the location of the jig plunger housing (e.g., jig plunger housing 410) along jig length (e.g., jig length 405). This step can be accomplished by positioning jig plunger housing at a desired location along jig length and moving one or more plunger housing fasteners (e.g., plunger housing fasteners 476, 476') to the second position such that the one or more plunger housing fasteners are in contact, or substantially contacting, jig shaft (e.g., jig shaft 408).

Another optional step comprises introducing treatment material into the injection device. This step can be accomplished by passing the treatment material through the needle shaft lumen and hub lumen and into the barrel lumen of the injection device. Alternatively, a treatment material can be passed through the first barrel opening and a plunger can subsequently be advanced through first barrel opening and into barrel lumen.

Alternative to completing step 502, injection device can be preloaded within a jig to provide a controlled injection system.

Step 504 can be accomplished by locating the cavity (e.g., cavity formed in bone, bodily passage) and advancing the controlled injection system towards the cavity until the injection device distal end is disposed within the cavity.

Step 506 can be accomplished by advancing the jig of the controlled injection system towards the cavity until the jig distal end contacts, or substantially contacts, the cavity wall.

An optional step comprises confirming contact between the jig and the cavity wall. This step can be accomplished through tactile feedback received by the user of the controlled injection system when the jig contacts, or substantially contacts, the cavity wall, or through visualizing the contact using any suitable method of visualization.

Step 508 can be accomplished by placing a proximal force on any portion of the barrel of the injection device (e.g., barrel finger flanges 24). It is considered advantageous to complete this step while jig maintains contact with the cavity wall.

An optional step comprises confirming that treatment material is being introduced into cavity. This step can be accomplished by direct visualization of the treatment material or through any other suitable method of visualization.

Step 510 can be accomplished by removing the proximal force from a portion, or the entirety, of the barrel of the injection device (e.g., barrel finger flanges 24).

Step 512 can be accomplished by placing a force on the jig such that it is advanced away from the cavity wall.

Optional steps comprise introducing treatment material into the injection device again and repeating steps 502, 504, 506, 508, and/or 510.

While various injection device configurations, jig configurations, steps, alternative steps, and optional steps have been described above with respect to introducing a treatment material into a cavity having a cavity wall, these injection device configurations, jig configurations, steps, alternative steps, and optional steps can be included in, accomplished concurrently with, and/or accomplished in the alternative to, the methodologies, injection device configurations, jig configurations, steps, alternative steps, and/or optional steps described below with respect to exemplary method 600 and/or method 900.

Figure 14:
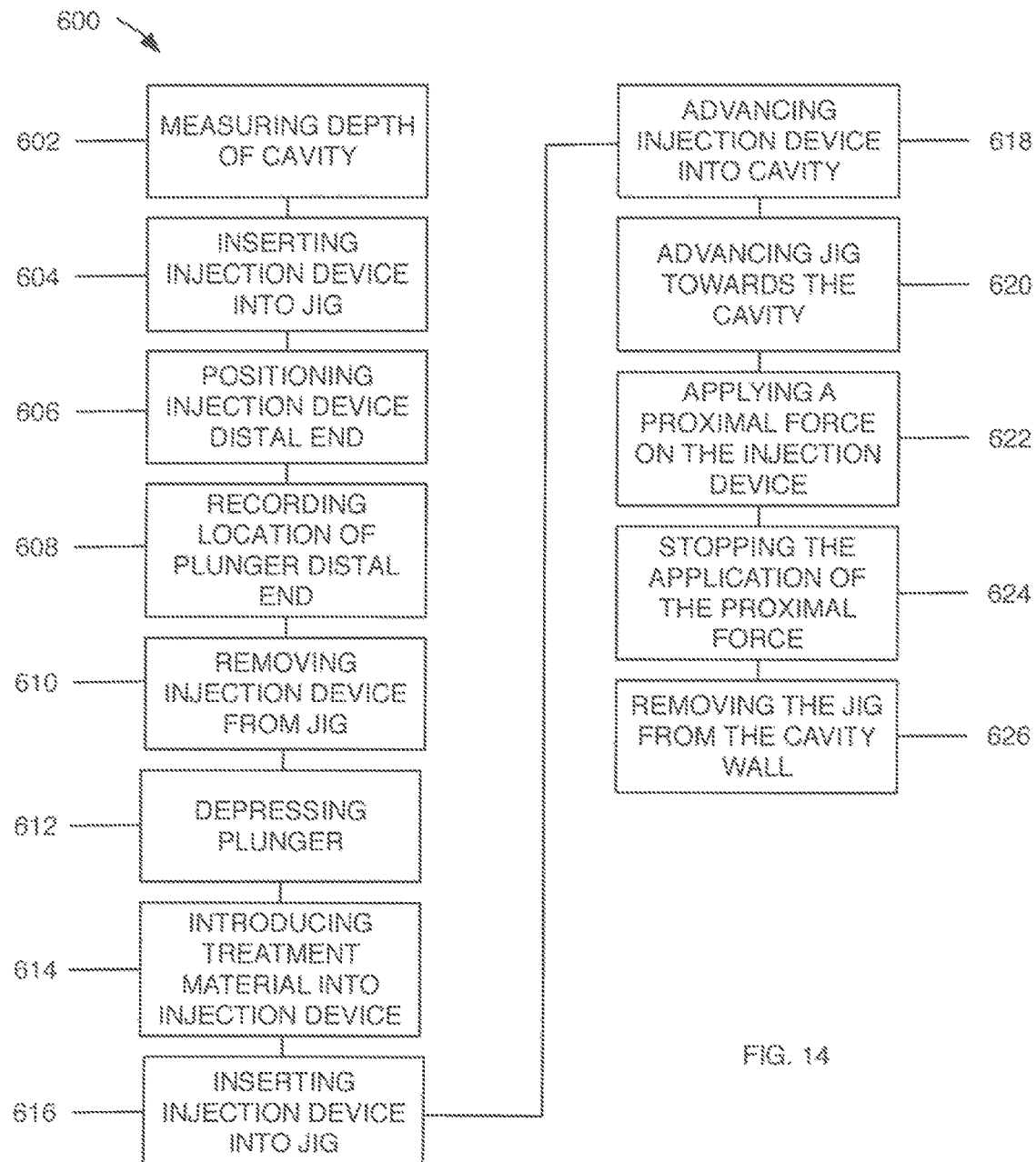
FIG. 14 is a flowchart representation of a second exemplary method of introducing a treatment material into a cavity.

FIG. 14 is a flowchart representation of another exemplary method 600 of introducing a treatment material into a cavity having a cavity wall.

A step 602 comprises measuring the depth of a cavity. Another step 604 comprises inserting an injection device having an injection device proximal end, an injection device distal end, a barrel, a needle, and a plunger into a jig having a jig proximal end and a jig distal end such that the injection device distal end is disposed distal to the jig distal end and the plunger is fixed relative to the jig. The barrel initially contains no treatment material. Another step 606 comprises positioning the injection device distal end (e.g., needle distal end) distal to the jig distal end a distance equal to, or substantially equal to, the measurement obtained in the step of measuring the cavity depth. Another step 608 comprises recording the location of the plunger distal end within the barrel while the injection device distal end is disposed distal to the jig distal end. Another step 610 comprises removing the injection device from the jig. Another step comprises 612 depressing the plunger such that the plunger distal end is disposed at, adjacent, or near, the barrel distal end. Another step 614 comprises introducing treatment material into the barrel such that the plunger distal end is disposed at, or near, the location within the barrel obtained in the step of recording the location of the plunger distal end position within the barrel while the injection device distal end is disposed distal to the jig distal end. Another step 616 comprises inserting the injection device into the jig such that the injection device distal end (e.g., needle distal end) is disposed distal to the jig distal end a distance equal to, or substantially equal to, the measurement obtained in the step of measuring the cavity depth. The barrel containing the treatment material. Another step 618 comprises advancing the injection device distal end into the cavity. Another step 620 comprises advancing the jig towards the cavity wall such that it contacts the cavity wall. Another step 622 comprises applying a proximal force on the barrel such that the barrel moves proximally with respect to the jig, injection device distal end is withdrawn in the cavity in a proximal direction, and the treatment material is introduced into the cavity. Another step 624 comprises stopping the application of the proximal force on the barrel. Another step 626 comprises removing the jig from the cavity wall.

Step 602 can be accomplished using any suitable method of measuring a cavity, and skilled artisans will be able to select a suitable method to measure a cavity based on various considerations, including the location of the cavity. Example methods of measuring a cavity considered suitable include, but are not limited to, direct visualization, using a measurement tool, x-ray, and any other method of measurement considered suitable for a particular application.

An optional step comprises recording the measurement obtained in step 602. Recording a measurement can be accomplished using any suitable method of recordation, and skilled artisans will be able to select suitable method of recordation to record a measurement according to a particular embodiment based on various considerations, including the type of measurement being obtained. Example methods of recordation considered suitable include, but are not limited to, inputting the measurement into a computer, writing the measurement on a form, having an individual memorize the measurement, and any other method of recordation considered suitable for a particular application.

Step 604 can be accomplished by inserting the plunger proximal end of an injection device (e.g., plunger proximal end 40) within a jig plunger housing (e.g., jig plunger housing 110) and the barrel distal end (e.g., barrel distal end 20) and/or needle hub (e.g., needle hub 54) within a head opening of a jig (e.g., head opening 120). In this step the barrel does not contain any treatment material.

Step 606 can be accomplished by measuring the distance between the injection device distal end and jig distal end to confirm that the injection device distal end is positioned a distance equal to, or substantially equal to, the measurement obtained in step 602.

Step 608 can be accomplished using any suitable method of recordation, and skilled artisans will be able to select suitable method of recordation to record a measurement according to a particular embodiment based on various considerations, including the type of measurement being obtained. Example methods of recordation considered suitable include, but are not limited to, inputting the measurement into a computer, writing the measurement on a form, having an individual memorize the measurement, and any other method of recordation considered suitable for a particular application.

Step 610 can be accomplished by removing the plunger proximal end of an injection device (e.g., plunger proximal end 40) from the jig plunger housing (e.g., jig plunger housing 110) and the barrel distal end (e.g., barrel distal end 20) and/or needle hub (e.g., needle hub 54) from the head opening of a jig (e.g., head opening 120).

Step 612 can be accomplished by applying a distal force on the plunger until the plunger distal end is disposed at, adjacent, or near, the barrel distal end. Alternatively, while the injection device is disposed within the jig, the barrel of the injection device can be advanced proximally such that the plunger distal end is disposed at, adjacent, or near, the barrel distal end.

Step 614 can be accomplished by inserting the injection device distal end into a container that houses the treatment material and applying a proximal force on the plunger until the plunger distal end is disposed at, or near, the location within the barrel obtained in the step of recording the location of the plunger distal end position within the barrel while the injection device distal end is disposed distal to the jig distal end.

Step 616 can be accomplished by inserting the plunger proximal end of an injection device (e.g., plunger proximal end 40) within a jig plunger housing (e.g., jig plunger housing 110) and the barrel distal end (e.g., barrel distal end 20) and/or needle hub (e.g., needle hub 54) within a head opening of a jig (e.g., head opening 120). In this step the barrel contains treatment material.

Steps 618, 620, 622, 624, and 626 can be accomplished as described above with respect to steps 504, 506, 508, 510, and 512.

Optional steps comprise repeating steps 602, 604, 606, 608, 610, 612, 614, 616, 618, 620, 622, 624, and/or 626. For example, after completing step 626, steps 610, 612, 614, 616, 618, 620, 622, 624, and/or 626 can be repeated.

While various injection device configurations, jig configurations, steps, alternative steps, and optional steps have been described above with respect to introducing a treatment material into a cavity having a cavity wall, these injection device configurations, jig configurations, steps, alternative steps, and optional steps can be included in, accomplished concurrently with, and/or accomplished in the alternative to, the methodologies, injection device configurations, jig configurations, steps, alternative steps, and/or optional steps described above with respect to exemplary method 500 and/or below with respect to exemplary method 900.

Figure 15:
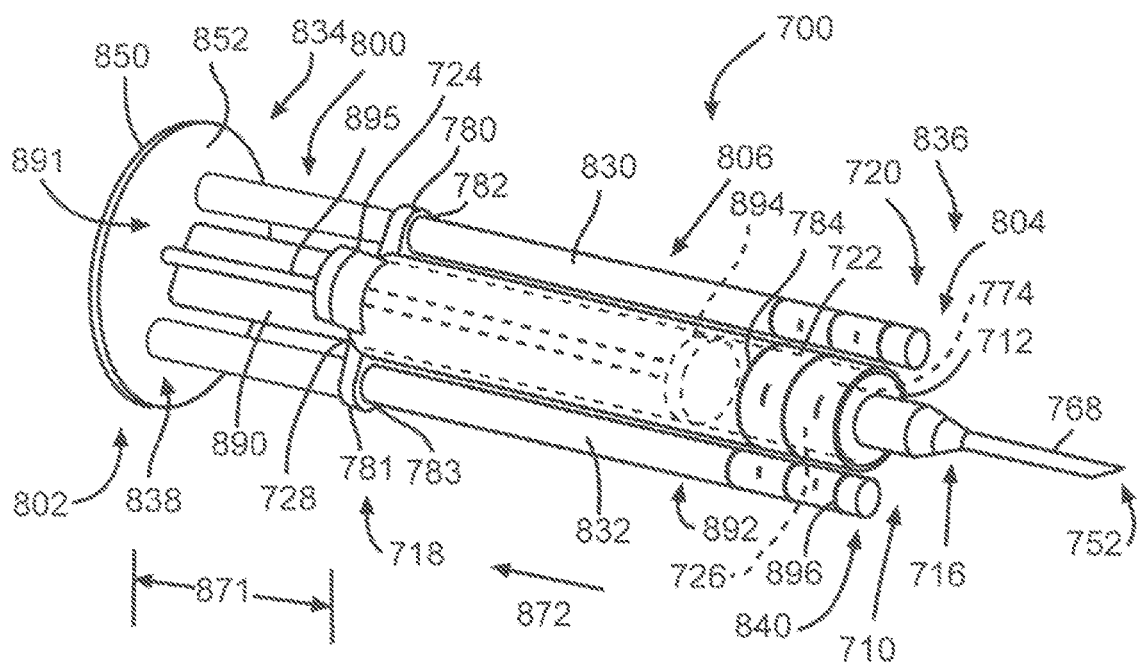
FIG. 15 is a perspective view of a first alternative controlled injection system in the first configuration.
Figure 16:
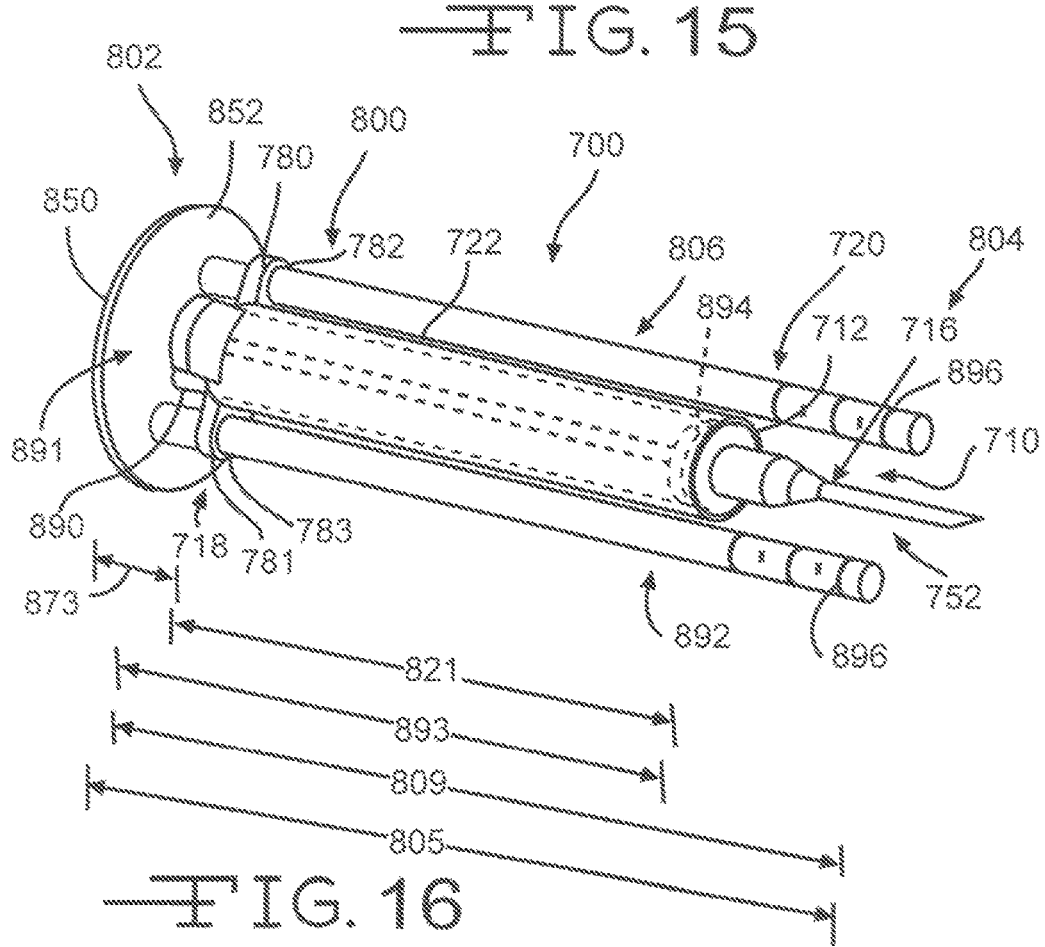
FIG. 16 is a perspective view of the controlled injection system illustrated in FIG. 15 in the second configuration.

FIGS. 15 and 16 illustrate a first alternative controlled injection system 700 comprising a syringe 710 and a jig 800. Controlled injection system 700 is similar to controlled injection system 300 illustrated in FIGS. 6, 7, 8, and 9, and described above, except as detailed below. With respect to syringe 710, reference numbers in FIGS. 15 and 16 refer to the same structural element or feature referenced by the same number in FIG. 1, offset by 700. With respect to jig 800, reference numbers in FIGS. 15 and 16 refer to the same structural element or feature referenced by the same number in FIGS. 2, 3, and 4, offset by 700.

In the illustrated embodiment, alternative to syringe 710 including a plunger, jig 800 includes a jig plunger 890 that is fixed relative to jig 800. In addition, in the illustrated embodiment, syringe 710 includes a plurality of indicia 784, jig 800 omits the inclusion of a jig head (e.g., jig head 106) and jig plunger housing (e.g., jig plunger housing 110), and jig 800 includes a plurality of indicia 896. Thus, syringe 710 comprises a barrel 712 and needle 716 and jig 800 comprises a jig proximal end 802, jig distal end 804, jig length 805, and a jig shaft 806.

Barrel 712 is similar to barrel 12 illustrated in FIG. 1, except that barrel 712 includes a first protuberance 780, a second protuberance 781, and a plurality of indicia 784 disposed along barrel length 821. The plurality of indicia has been omitted from FIG. 16 for clarity. Each of the first protuberance 780 and second protuberance 781 extends radially outward from barrel wall 722. First protuberance 780 defines a first protuberance aperture 782 that extends through the wall of first protuberance 780 and second protuberance 781 defines a second protuberance aperture 783 that extends through the wall of second protuberance 781. In the illustrated embodiment, each of the first protuberance aperture 782 and second protuberance aperture 783 is disposed parallel, or substantially parallel, to first barrel opening 728. First protuberance aperture 782 is adapted to receive first shaft arm 830 and second protuberance aperture 783 is adapted to receive second shaft arm 832.

A first indicium of the plurality of indicia 784 is disposed a first distance from a second indicium of the plurality of indicia 784 and a third indicium of the plurality of indicia 784 is disposed a second distance from the second indicium of the plurality of indicia 784. The first distance and the second distance are equal, or substantially equal, to one another. Thus, in the illustrated embodiment, each indicium of the plurality of indicia 784 is disposed at an equal, or substantially equal, distance from another indicium of the plurality of indicia 784. It is considered advantageous to include a plurality of indicia 784 along barrel length 721 at least because it provides a mechanism for determining the amount treatment material being stored within the barrel lumen and/or introduced into a cavity. Any suitable distance can be used to separate each indicium of the plurality of indicia 784 from another indicium of the plurality of indicia 784, and skilled artisans will be able to select a suitable distance according to a particular embodiment based on various considerations, including the size of the cavity being treated. The distance used to separate each indicium of a plurality of indicia from another indicium of the plurality of indicia can be measured using any suitable form of measurement. Example forms of measurement considered suitable include, but are not limited to, millimeters, centimeters, and any other form of measurement considered suitable for a particular application.

While a first protuberances 780 and second protuberance 781 have been illustrated and described, any suitable number of protuberances can be included on a barrel and skilled artisans will be able to select a suitable number of protuberances to include on a barrel according to a particular embodiment based on various considerations, including the structural arrangement of a jig shaft. Example number of protuberances considered suitable to include on a barrel include, but are not limited to, one, at least one, two, a plurality, three, four, and any other number considered suitable for a particular application. In addition, each protuberance can define any suitable number of apertures, and skilled artisans will be able to select a suitable number of apertures to include on a protuberance according to a particular embodiment based on various considerations, including the structural arrangement of a jig shaft. Example number of apertures considered suitable to include on a protuberance include, but are not limited to, one, at least one, two, a plurality, three, four, and any other number considered suitable for a particular application.

In the illustrated embodiment, jig 800 omits the inclusion of a jig head and alternative to including a jig plunger housing (e.g., jig plunger housing 110), jig 800 has a jig proximal end 802 that has a proximal surface 850 and a distal surface 852 from which each of jig shaft 806 and jig plunger 890 extends. Jig 800 also includes a plurality of indicia 896 disposed along a jig shaft length 809 that extends from first shaft arm proximal end 834 and second shaft arm proximal end 838 to first shaft arm distal end 836 and second shaft arm distal end 840. Jig plunger 890 comprises a jig plunger proximal end 891, jig plunger distal end 892, jig plunger length 893, jig plunger tip 894, and jig plunger body 895. Jig plunger proximal end 891 is disposed on and attached to distal surface 852 and jig plunger length 893 extends from distal surface 852 towards jig distal end 804 to jig plunger distal end 892. Jig plunger length 893 is less than jig shaft length 809 and extends from distal surface 852 to jig plunger distal end 892. Jig plunger tip 894 is attached to jig plunger distal end 892 and is adapted to be received within barrel lumen 726.

It is considered advantageous for barrel length 821 and jig plunger length 893 to be less than jig shaft length 809 at least because this configuration advantageously allows for a portion, or the entirety, of a treatment material to be stored within barrel lumen 726 when needle distal end 752 is disposed distal to jig distal end 804. In addition, this configuration is considered advantageous at least because it provides a mechanism for contacting jig distal end 804 with a surface such that it acts as a mechanical stop while allowing needle distal end 752 to be introduced into a cavity, as described in more detail herein.

A first indicium of the plurality of indicia 896 is disposed a first distance from a second indicium of the plurality of indicia 896 and a third indicium of the plurality of indicia 896 is disposed a second distance from the second indicium of the plurality of indicia 896. The first distance and the second distance are equal, or substantially equal, to one another. Thus, in the illustrated embodiment, each indicium of the plurality of indicia 896 is disposed at an equal, or substantially equal, distance from another indicium of the plurality of indicia 896. It is considered advantageous to include a plurality of indicia 896 along jig shaft length 809 at least because it provides a mechanism for determining the amount treatment material being stored within the barrel lumen and/or introduced into a cavity and for determining the length and/or depth of a cavity being filled with a treatment material. Any suitable distance can be used to separate each indicium of the plurality of indicia 896 from another indicium of the plurality of indicia 896, and skilled artisans will be able to select a suitable distance according to a particular embodiment based on various considerations, including the size of the cavity being treated. The distance used to separate each indicium of a plurality of indicia from another indicium of the plurality of indicia can be measured using any suitable form of measurement. Example forms of measurement considered suitable include, but are not limited to, millimeters, centimeters, and any other form of measurement considered suitable for a particular application.

While each indicium of the plurality of indicia 784 disposed on barrel 712 and each indicium of the plurality of indicia 896 disposed on jig 800 has been illustrated and described as disposed at an equal, or substantially equal, distance from another indicium of the plurality of indicia, any suitable distance can be disposed between each indicium of a plurality of indicia and another indicium of the plurality of indicia. Skilled artisans will be able to select a suitable distance between each indicium of a plurality of indicia and another indicium of the plurality of indicia according to a particular embodiment based on various considerations, including the size of the cavity being treated. Example distances considered suitable between each indicium of a plurality of indicia and another indicium of the plurality of indicia include, but are not limited to, distances that are equal, or substantially equal, to one another, distances that vary from one another, and any other distance considered suitable for a particular application.

Barrel 712 is slidably disposed over jig shaft 806 and jig plunger 890 such that barrel 712 is moveable along jig plunger length 893. Thus, barrel 712 is adapted to move axially along jig plunger length 893. Jig plunger tip 894 is configured to prevent, or substantially prevent, treatment material from passing proximally beyond jig plunger tip 894 when in use (e.g., disposed within barrel lumen 726). For example, when a treatment material is stored within barrel lumen 726, such as cement, and barrel 712 is moved proximally over jig plunger 890, the treatment material within barrel lumen 726 is forced distally through needle 716. This can be accomplished by configuring jig plunger tip 894 to have an outside diameter that is equal to, substantially equal to, or greater than, the inside diameter of barrel 712. Thus, jig plunger tip 894 is adapted to provide a moveable sealing engagement with barrel 712.

FIG. 15 illustrates controlled injection system 700 in a first configuration and FIG. 16 illustrates controlled injection system 700 in a second configuration. In the first configuration, syringe 710 is disposed on jig 800 such that needle distal end 752 is disposed distal to jig distal end 804. In the first configuration, plunger tip 894 is disposed proximal to barrel distal end 720, jig proximal end 802 is disposed proximal to barrel proximal end 718 a first distance 871, and treatment material 774 is stored in barrel lumen 726. In addition, needle distal end 752 is disposed distal to jig distal end 804. By placing a proximal force on barrel 712 (e.g., barrel finger flanges 724) in the direction of arrow 872, syringe 710 can be moved to the second configuration, as shown in FIG. 16, and treatment material 774 can be passed through barrel lumen 726 and needle shaft lumen 768.

In the second configuration, plunger tip 894 is disposed at, or near, barrel distal end 720, jig proximal end 802 is disposed proximal to barrel proximal end 718 a second distance 873 from barrel proximal end 718 that is less than the first distance 871, and a portion, or the entirety, of treatment material 774 has been expelled from barrel lumen 726. Thus, when syringe 710 is moved from the first configuration to the second configuration, treatment material 774 that is stored within barrel lumen 726 is passed through barrel lumen 726 and needle 716. In addition, in the second configuration, each of the barrel 712 and/or needle 716 has been withdrawn proximally along jig length 805 such that needle distal end 752 has been advanced proximally and is positioned at, or near, jig distal end 804.

While needle distal end 752 has been illustrated and described as positioned at, or near, jig distal end 804 when controlled injection system 800 and/or syringe 710 is in the second configuration, the needle distal end of a syringe can be positioned at any suitable location along a jig length, or beyond a jig length, when a controlled injection system and/or syringe is the first configuration or second configuration. Skilled artisans will be able to select a suitable position for a needle distal end with respect to a controlled injection system according to a particular embodiment based on various considerations, including the depth of a cavity that is being treated. Example positions considered suitable for a needle distal end of an injection device when a controlled injection system and/or syringe is in the first configuration or second configuration include, but are not limited to, distal to a jig distal end, at a jig distal end, near a jig distal end, and proximal to a jig distal end.

In use, jig distal end 804 contacts a surface (e.g., bone) that forms a cavity. The interaction between the surface that forms the cavity and jig distal end 804 acts as a mechanical stop preventing distal advancement of jig 800 beyond where jig distal end 804 contacts the surface. Thus, controlled injection system 800 provides a mechanism for advancing a needle distal end 752 into a cavity a predetermined distance from jig distal end 804 while also providing a mechanism for limiting distal advancement of jig distal end 804 beyond the surface that forms the cavity. The distance a needle 716 is advanced into a cavity is based on the structural configuration of jig 800 (e.g., jig shaft 806, jig distal end 804) and/or the structural arrangement of the injection device being used.

Barrel lumen 726 and jig plunger 890 can have any suitable diameter. It is considered advantageous for jig plunger 890 and/or jig plunger tip 894 to complement the diameter of barrel lumen 726 such that a moveable sealing engagement can be accomplished between barrel 712 and jig plunger tip 894, as described herein. Barrel lumen 726 and jig plunger tip 894 can comprise a diameter that is equal, substantially equal, or complementary, to the diameter of a cavity that is being treated. This configuration is considered advantageous at least because it provides a mechanism for introducing an amount of treatment material into barrel lumen 726 that is equal to, substantially equal to, or approximates, an amount necessary to fill the length and/or depth of the cavity being treated. For example, when barrel lumen 726 and jig plunger tip 894 comprise a diameter that is equal, substantially equal, or complementary, to the diameter of a cavity that is being treated, treatment material can be introduced into barrel lumen 726 such that the distance between barrel distal end 820 and jig plunger tip 894 is equal to, substantially equal to, or approximates, the length and/or depth of the cavity being treated or desired to be treated.

The configuration of jig 800 is considered advantageous because jig plunger 890 is fixed relative to the jig 800 which, when jig distal end 804 is in contact with a surface that defines a cavity, allows for controlled injection of a treatment material into a cavity by advancing syringe 710 proximally along jig length 805. The configuration of jig 800 is also considered advantageous at least because it allows for treatment material 774 stored within barrel lumen 726 to be introduced into a cavity continuously, or substantially continuously, while simultaneously withdrawing needle distal end 752 from the cavity. This prevents, or substantially prevents, disruption in treatment material 774 as it is being introduced into the cavity. The configuration of jig 800 is also considered advantageous at least because it provides a mechanism for controlling the placement of treatment material 774 within a cavity. For example, some cavities can have a distal end formed of a soft tissue for which it is not desired to introduce treatment material. The configuration of jig 800 provides a mechanical stop to distal advancement of a needle distal end within a cavity such that treatment material can be positioned within the cavity at a desired point of treatment as the barrel of an injection device is advanced proximally.

Figure 17:
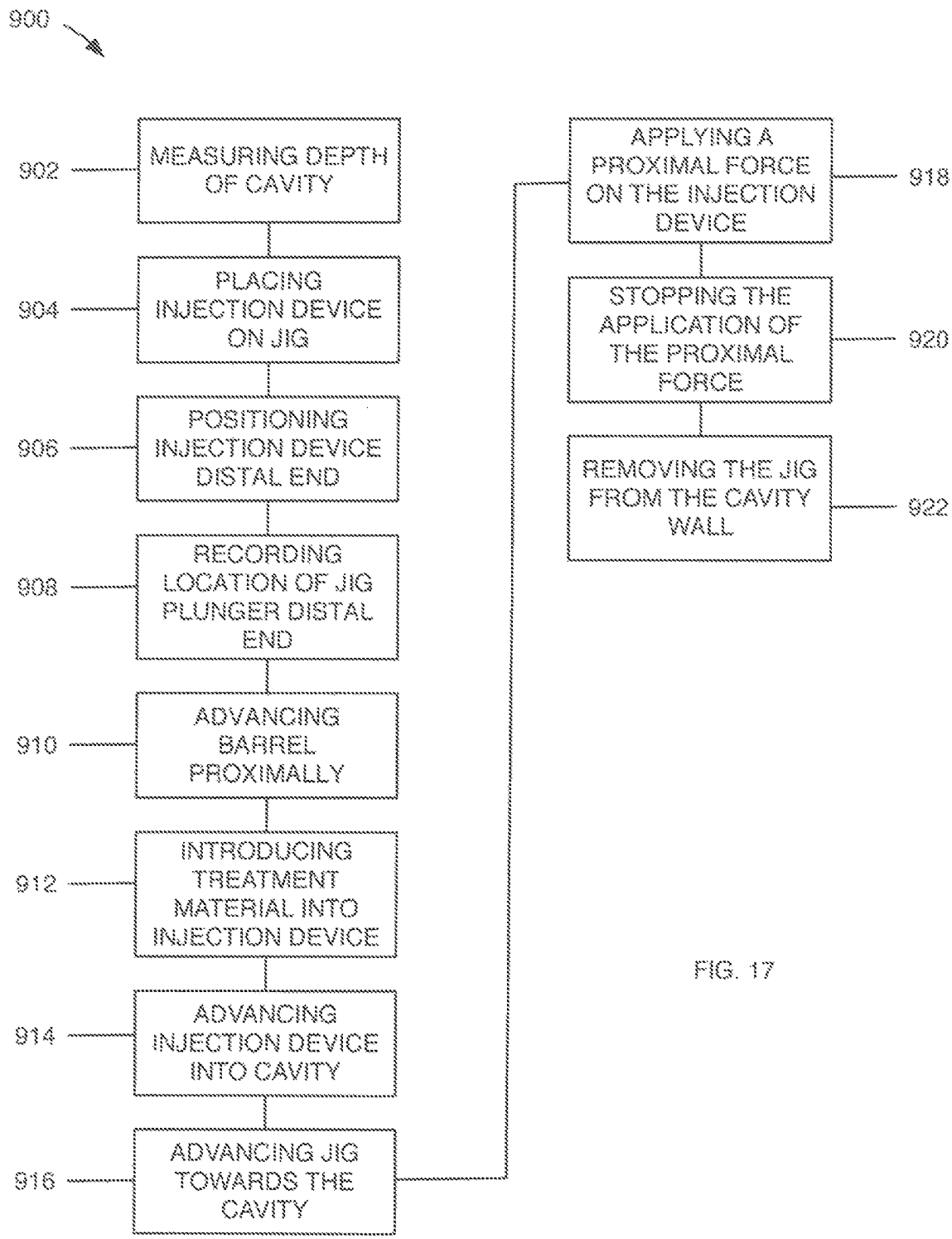
FIG. 17 is a flowchart representation of a third exemplary method of introducing a treatment material into a cavity.

FIG. 17 is a flowchart representation of another exemplary method 900 of introducing a treatment material into a cavity having a cavity wall.

A step 902 comprises measuring the depth of a cavity. Another step 904 comprises placing an injection device having an injection device proximal end, an injection device distal end, a barrel, and a needle on a jig having a jig proximal end, a jig distal end, and a jig plunger fixed relative to the jig such that the injection device distal end is disposed distal to the jig distal end. The barrel initially contains no treatment material. Another step 906 comprises positioning the injection device distal end (e.g., needle distal end) distal to the jig distal end a distance equal to, or substantially equal to, the measurement obtained in the step of measuring the cavity depth. Another step 908 comprises recording the location of the jig plunger distal end within the barrel while the injection device distal end is disposed distal to the jig distal end. Another step comprises 910 advancing the barrel of the injection device proximally such that the jig plunger distal end is disposed at, adjacent, or near, the barrel distal end. Another step 912 comprises introducing treatment material into the barrel such that the jig plunger distal end is disposed at, or near, the location within the barrel obtained in the step of recording the location of the jig plunger distal end position within the barrel while the injection device distal end is disposed distal to the jig distal end. Another step 914 comprises advancing the injection device distal end into the cavity. Another step 916 comprises advancing the jig towards the cavity wall such that it contacts the cavity wall. Another step 918 comprises applying a proximal force on the barrel such that the barrel moves proximally with respect to the jig, injection device distal end is withdrawn in the cavity in a proximal direction, and the treatment material is introduced into the cavity. Another step 920 comprises stopping the application of the proximal force on the barrel. Another step 922 comprises removing the jig from the cavity wall.

Methodology 900 is similar to methodology 600, except that it is performed with controlled injection device 700. While a particular controlled injection device has been described as performing methodology 900, any suitable controlled injection device, jig, and/or injection device can be used to accomplish methodology 900, or any other methodology described herein. Skilled artisans will be able to select a suitable controlled injection device, jig, and/or injection device to accomplish a methodology according to a particular embodiment based on various considerations, including the structural configuration of a cavity and/or cavity wall. Example controlled injection devices, jig, and injection devices considered suitable to accomplish one or more of the methodologies described herein include, but are not limited to, controlled injection device 300, controlled injection device 700, jig 100, jig 200, jig 400, injection device 10, and any other controlled injection device, jig, and/or injection device considered suitable for a particular application.

While various injection device configurations, jig configurations, steps, alternative steps, and optional steps have been described above with respect to introducing a treatment material into a cavity having a cavity wall, these injection device configurations, jig configurations, steps, alternative steps, and optional steps can be included in, accomplished concurrently with, and/or accomplished in the alternative to, the methodologies, injection device configurations, jig configurations, steps, alternative steps, and/or optional steps described above with respect to exemplary method 500 and/or exemplary method 600.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A controlled injection system comprising:
   an injection device having a barrel, a plunger partially disposed within the barrel, and a needle attached to the barrel, the barrel having an outside diameter and an exterior surface;
   a jig having a jig proximal end, a jig distal end, a jig length extending from the jig proximal end to the jig distal end, and the injection device disposed within the jig, the jig comprising:
      a jig head having a head proximal end, head distal end, and a head body defining an interior surface, the interior surface directly contacting the exterior surface of the barrel and defining a head opening adapted to receive a portion of the injection device, the head opening extending from the head proximal end to the head distal end, the head opening comprising a diameter at the head distal end that is less than the outside diameter of the barrel;
      a jig shaft extending from the jig head and towards the jig proximal end, the jig shaft having a shaft proximal end and a shaft distal end; and
      a jig plunger housing fixed to the jig shaft such that the plunger is fixed relative to the jig and is prevented from moving axially along the jig length, the jig plunger housing having a plunger housing proximal end, a plunger housing distal end, and a plunger housing body defining a plunger housing recess extending into the plunger housing body, the plunger housing recess adapted to receive a portion of the plunger.

2. The controlled injection system of claim 1, wherein the head opening has a head opening first portion and a head opening second portion, the head opening first portion extending from the head proximal end towards the head distal end, the head opening second portion extending from the head distal end towards the head proximal end;
   wherein the head opening first portion comprises a first diameter;
   wherein the head opening second portion comprises a second diameter; and
   wherein the first diameter is different than the second diameter.

3. The controlled injection system of claim 2, wherein the first diameter is greater than the second diameter.

4. The controlled injection system of claim 3, wherein the head opening first portion has a substantially constant diameter; and
   wherein the head opening second portion tapers from a location proximal to the head distal end to the head distal end.

5. The controlled injection system of claim 1, wherein the head opening has a head opening first portion, a head opening second portion, and a head opening third portion, the head opening first portion extending from the head proximal end towards the head distal end, the head opening second portion extending between the head proximal end and the head distal end, and the head opening third portion extending from the head distal end towards the head proximal end;
   wherein the head opening first portion comprises a first diameter;
   wherein the head opening second portion comprises a second diameter;
   wherein the head opening third portion comprises a third diameter; and
   wherein the first diameter is different than the second diameter and the second diameter is different than the third diameter.

6. The controlled injection system of claim 5, wherein the first diameter is greater than the second diameter; and
   wherein the second diameter is greater than the third diameter.

7. A controlled injection system comprising:
   an injection device having a barrel, a plunger partially disposed within the barrel, and a needle attached to the barrel, the barrel having an outside diameter and an exterior surface;
   a jig having a jig proximal end, a jig distal end, a jig length extending from the jig proximal end to the jig distal end, and the injection device disposed within the jig, the jig comprising:
      a jig head having a head proximal end, head distal end, and a head body defining an interior surface, the interior surface directly contacting the exterior surface of the barrel and defining a head opening adapted to receive a portion of the injection device, the head opening extending from the head proximal end to the head distal end, the head opening comprising a diameter at the head distal end that is less than the outside diameter of the barrel;
      a jig shaft extending from the jig head and towards the jig proximal end, the jig shaft having a shaft proximal end and a shaft distal end; and
      a jig plunger housing fixed to the jig shaft such that the plunger is fixed relative to the jig and is prevented from moving axially along the jig length, the jig plunger housing having a plunger housing proximal end, a plunger housing distal end, and a plunger housing body defining a plunger housing recess extending into the plunger housing body, the plunger housing recess adapted to receive a portion of the plunger and having a plunger housing recess first portion and a plunger housing recess second portion, the plunger housing recess first portion extending from the plunger housing distal end towards the plunger housing proximal end, the plunger housing recess second portion extending from the plunger housing first portion towards the plunger housing proximal end, the plunger housing recess first portion comprising a plunger housing first width measured along the plunger housing distal end, the plunger housing recess second portion comprising a plunger housing second width measured along the plunger housing distal end, the plunger housing first width being different from the plunger housing second width.

8. The controlled injection system of claim 7, wherein the plunger housing second width is greater than the plunger housing first width.

9. The controlled injection system of claim 7, wherein the head opening has a head opening first portion and a head opening second portion, the head opening first portion extending from the head proximal end towards the head distal end, the head opening second portion extending from the head distal end towards the head proximal end;
    wherein the head opening first portion comprises a first diameter;
    wherein the head opening second portion comprises a second diameter; and
    wherein the first diameter is different than the second diameter.

10. The controlled injection system of claim 9, wherein the first diameter is greater than the second diameter.

11. The controlled injection system of claim 10, wherein the head opening first portion has a substantially constant diameter; and
    wherein the head opening second portion tapers from a location proximal to the head distal end to the head distal end.

12. The controlled injection system of claim 7, wherein the head opening has a head opening first portion, a head opening second portion, and a head opening third portion, the head opening first portion extending from the head proximal end towards the head distal end, the head opening second portion extending between the head proximal end and the head distal end, and the head opening third portion extending from the head distal end towards the head proximal end;
    wherein the head opening first portion comprises a first diameter;
    wherein the head opening second portion comprises a second diameter;
    wherein the head opening third portion comprises a third diameter; and
    wherein the first diameter is different than the second diameter and the second diameter is different than the third diameter.

13. The controlled injection system of claim 12, wherein the first diameter is greater than the second diameter; and
    wherein the second diameter is greater than the third diameter.

14. The controlled injection system of claim 1, wherein the barrel has barrel finger flanges;
    wherein the jig head, the jig shaft, and the jig housing define a jig opening extending along the jig length between the jig proximal end and the jig distal end; and
    wherein the barrel finger flanges are disposed within and extend radially outward of the jig opening.

15. The controlled injection system of claim 1, wherein the jig shaft is fixed to the jig head.

* * * * *